United States Patent
Richards-Kortum et al.

(10) Patent No.: US 6,697,666 B1
(45) Date of Patent: Feb. 24, 2004

(54) APPARATUS FOR THE CHARACTERIZATION OF TISSUE OF EPITHELIAL LINED VISCUS

(75) Inventors: Rebecca Richards-Kortum, Austin, TX (US); Michele Follen Mitchell, Houston, TX (US); Urs Utzinger, Bachenbülach (CH)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/519,153

(22) Filed: Mar. 6, 2000

Related U.S. Application Data

(62) Division of application No. 08/693,471, filed on Jun. 22, 1999, now abandoned.

(51) Int. Cl.[7] .................................................. A61B 5/00
(52) U.S. Cl. ........................... 600/478; 604/27; 604/48
(58) Field of Search .................... 600/473, 475–479, 600/104, 156, 182, 342; 604/27, 48

(56) References Cited

U.S. PATENT DOCUMENTS

| | | | |
|---|---|---|---|
| 4,556,057 A | 12/1985 | Hiruma et al. | 128/303.1 |
| 4,648,892 A | 3/1987 | Kittrell et al. | 65/4.21 |
| 4,675,529 A | 6/1987 | Kushida | 250/458.1 |
| 4,755,684 A | 7/1988 | Leiner et al. | 250/461.1 |
| 4,768,513 A | 9/1988 | Suzuki | 128/634 |
| 4,786,813 A | 11/1988 | Svanberg et al. | 250/461.1 |
| 4,913,142 A | 4/1990 | Kittrell et al. | 606/7 |
| 4,930,516 A | 6/1990 | Alfano et al. | 128/665 |
| 4,967,745 A | 11/1990 | Hayes et al. | 128/303.1 |
| 5,003,977 A | 4/1991 | Suzuki et al. | 128/633 |

(List continued on next page.)

FOREIGN PATENT DOCUMENTS

| | | |
|---|---|---|
| EP | 0 606 987 A1 | 8/1994 |
| JP | 1151436 | 6/1989 |
| WO | WO 88/05908 | 8/1988 |
| WO | WO 94/26168 | 11/1994 |
| WO | WO 95/26673 | 10/1995 |
| WO | WO 96/02184 | 2/1996 |
| WO | WO 96/28084 | 9/1996 |

OTHER PUBLICATIONS

Alfano et al., "Laser Induced Fluorescence Spectroscopy from Native Cancerous and Normal Tissue," *IEEE Journal of Quantum Electronics*, QE–20(12):1507–1511, 1984.

(List continued on next page.)

*Primary Examiner*—Ruth S. Smith
(74) *Attorney, Agent, or Firm*—Fulbright & Jaworski, LLP

(57) ABSTRACT

A method and apparatus for characterizing tissue of epithelial lined viscus in vivo including, for example, the endocervical canal. The method comprises illuminating an interior surface of the viscus with electromagnetic radiation wavelengths to produce a plurality of fluorescence intensity spectra, detecting a plurality of emission wavelengths from the fluorescence intensity spectra, and characterizing the epithelial viscus tissue as a function of the emission wavelengths. The apparatus includes a light source of emitting a plurality of electromagnetic radiation wavelengths, an optical probe connected to the light source, the probe being adapted to apply the plurality of electromagnetic radiation wavelengths to an interior surface of epithelial viscus tissue under test and to gather fluorescence emitted from the tissue, a detector connected to the probe for detecting at least one fluorescence spectrum emitted from the tissue under test and a programmed computer connected to the detector for processing the at least one fluorescence spectrum according to a predetermined algorithm to characterize the tissue under test.

6 Claims, 17 Drawing Sheets

U.S. PATENT DOCUMENTS

| | | | |
|---|---|---|---|
| 5,009,655 A | 4/1991 | Daignault, Jr. et al. | 606/7 |
| 5,014,707 A | 5/1991 | Schwarz et al. | 128/633 |
| 5,026,368 A | 6/1991 | Adair | 606/15 |
| 5,034,010 A | 7/1991 | Kittrell et al. | 606/15 |
| 5,036,853 A | 8/1991 | Jeffcoat et al. | 128/634 |
| 5,042,494 A | 8/1991 | Alfano | 128/665 |
| 5,046,501 A | 9/1991 | Crilly | 128/665 |
| 5,062,431 A | 11/1991 | Potter | 128/665 |
| 5,078,711 A | 1/1992 | Kakami et al. | 606/16 |
| 5,092,331 A | 3/1992 | Nakamura et al. | 128/634 |
| 5,104,392 A | 4/1992 | Kittrell et al. | 606/15 |
| 5,106,387 A | 4/1992 | Kittrell et al. | 606/15 |
| 5,115,137 A | 5/1992 | Andersson-Engels et al. | 250/461.2 |
| 5,125,404 A | 6/1992 | Kittrell et al. | 128/634 |
| 5,131,398 A | 7/1992 | Alfano et al. | 128/665 |
| 5,192,278 A | 3/1993 | Hayes et al. | 606/15 |
| 5,199,431 A | 4/1993 | Kittrell et al. | 128/634 |
| 5,201,318 A | 4/1993 | Rava et al. | 128/665 |
| 5,251,613 A | 10/1993 | Adair | 128/6 |
| 5,261,410 A | 11/1993 | Alfano et al. | 128/664 |
| 5,280,788 A | 1/1994 | Janes et al. | 128/665 |
| 5,290,275 A | 3/1994 | Kittrell et al. | 606/15 |
| 5,303,026 A | 4/1994 | Strobl et al. | 356/318 |
| 5,304,173 A | 4/1994 | Kittrell et al. | 606/15 |
| 5,318,023 A | 6/1994 | Vari et al. | 128/633 |
| 5,318,024 A | 6/1994 | Kittrell et al. | 128/634 |
| 5,345,941 A | 9/1994 | Rava et al. | 128/665 |
| 5,353,791 A | 10/1994 | Tamura et al. | 128/633 |
| 5,377,676 A | 1/1995 | Vari et al. | 128/634 |
| 5,383,467 A | 1/1995 | Auer et al. | 128/664 |
| 5,408,996 A | 4/1995 | Salb | 128/633 |
| 5,419,323 A | 5/1995 | Kittrell et al. | 128/653.1 |
| 5,421,337 A | 6/1995 | Richards-Kortum et al. | 128/665 |
| 5,421,339 A | 6/1995 | Ramanujam et al. | 128/665 |
| 5,439,000 A | 8/1995 | Gunderson et al. | 128/664 |
| 5,441,053 A | 8/1995 | Lodder et al. | 128/664 |
| 5,450,125 A | 9/1995 | Ulich et al. | 348/31 |
| 5,450,857 A | 9/1995 | Garfield et al. | 128/778 |
| 5,452,723 A | 9/1995 | Wu et al. | 128/664 |
| 5,456,260 A | 10/1995 | Kollias et al. | 128/665 |
| 5,467,767 A | 11/1995 | Alfano et al. | 128/665 |
| 5,496,305 A | 3/1996 | Kittrell et al. | 606/15 |
| 5,507,287 A | 4/1996 | Palcic et al. | 128/633 |
| 5,552,134 A | 9/1996 | Morgan et al. | 424/9.61 |
| 5,764,840 A * | 6/1998 | Wach | 385/123 |
| 5,773,835 A | 6/1998 | Sinofsky | 250/462.1 |
| 5,983,125 A * | 11/1999 | Alfano et al. | 600/478 |
| 6,296,608 B1 * | 10/2001 | Daniels et al. | 600/478 |

OTHER PUBLICATIONS

Avrillier et al., "XeC1 Excimer Laser–Induced Autofluorescence Spectroscopy for Human Cerebral Tumours Diagnosis: Preliminary Study," SPIE, 1894:177–186, 1993.

Bergeron et al., "Complete Fluorescence Spectrum of a Normal an Atherosclerotic Aorta," Can. J. Phys., 66:1035–1039, 1988.

Bosshart et al., "Fluorescence Spectroscopy for Identification of Atherosclerotic Tissue," Cardiovascular Research, 26:620–625, 1992.

Bottiroli et al., "Natural Fluorescence of Normal and Neoplastic Human Colon: A Comprehensive "ex vivo" Study," Lasers in Surgery & Medicine, 16(1):48–60, 1995.

Clarke et al., "Spectroscopic Characterization of Cardiovascular Tissue," Lasers in Surgery and Medicine, 8:45–59, 1988.

Deckelbaum et al., "Discrimination of Normal and Atherosclerotic Aorta by Laser–Induced Fluorescence," Lasers in Surgery and Medicine, 7:330–335, 1987.

Deckelbaum et al., "In–vivo Fluorescence Spectroscopy of Normal and Atherosclerotic Arteries," SPIE, 906:314–319, 1988.

D'Hallewin et al., "In Vivo Fluorescence Detection of Human Bladder Carcinoma Without Sensitizing Agents," Journal of the American Paraplegia Society, 17(4):161–164, 1994.

Edholm et al., "Tissue Identification During Needle Puncture by ReflectionSpectrophotometry, "Biol. Engng., 6:409–413, 1968.

Fiarman et al., "Differences in Laser–Induced Autofluorescence between Adenomatous and Hyperplastic Polps and Normal Confocal Mucosa by Confocal Microscopy," Digestive Disease & Sciences, 40(6):1261–1268, 1995.

Fitzmaurice et al., "Argon Ion Laser–Excited Autofluorescence in Normal and Atherosclerotic Aorta and Coronary Arteries: Morphologic Studies," American Heart Journal, 118(5):1028–1037, 1989.

Frank et al., "Characterization of Human Breast Biopsy Specimens with Near–IR Raman Spectroscopy," Anal. Chem., 66:319–326, 1994.

Ghadially and Neish, "Porphyrin Fluorescence of Experimentally Produced Squamous Cell Carcinoma," Nature, 188:1124, 1960.

Ghadially et al., "Mechanisms Involved in the Production of Red Fluorescence of Human and Experimental Tumours," Path. Bact., 85:77–92, 1963.

Glassman et al., "Excitation Spectroscopy of Malignant and Non–malignant Gynecological Tissues," Lasers in the Life Sciences, 6(2):99–106, 1994.

Glassman et al., "Time Resolved and Steady State Fluorescence Spectroscopy from Normal and Malignant Cultured Human Breast Cell Lines," Lasers in the Life Sciences, 6(2):91–98, 1994.

Gmitro et al., "Measurement Depth of Laser–Induced Tissue Fluorescence with Application to Laser Angioplasty," Applied Optics, 27(9):1844–1849, 1988.

Harries et al., "Diagnostic Imaging of the Larynx: Autofluorescence of Laryngeal Tumours Using the Helium–Cadmium Laser," The Journal of Laryngology and Otology, 109:108–110, 1995.

Hoyt et al., "Remote Biomedical Spectroscopic Imaging of Human Artery Wall," Lasers in Surgery and Medicine, 8:1–9, 1988.

Kittrell et al., "Diagnosis of Fibrous Arterial Atherosclerosis Using Fluorescence," Applied Optics, 24(15):2280–2281, 1985.

Kluftinger et al., "Detection of Squamous Cell Cancer and Pre–cancerous Lesions by Imaging of Tissue Autofluorescence in the Hamster Check Pouch Model," Surgical Oncology, 1:183–188, 1992.

Laifer et al., "Biochemical Basis for the Difference Between Normal and Atherosclerotic Arterial Fluorescence," Circulation, 80(6):1893–1901, 1989.

Lam et al., "Detection of Dysplasia and Carcinoma is situ with a Lung Imaging Fluorescence Endoscope Device," J. Thorac Cardiovasc. Surg., 105:1035–1040, 1993.

Leon et al., "Human Arterial Surface Fluorescence: Atherosclerotic Plaque Identification and Effects of Laser Atheroma Ablation," JACC, 12(1):94–102, 1988.

Liu et al., "Raman, Fluorescence, and Time–Resolved Light Scattering as Optical Diagnostic Techniques to Separate Diseased and Normal Biomedical Media," *J. Photochem. Photobiol. B: Biol.*, 16:187–209, 1992.

Lohmann et al., "In situ Differentiation Between Nevi and Malignant Melanomas by Fluorescence Measurements," *Naturwissenschaften*, 78:456–457, 1991.

Lohmann et al., "Fluorescence Studies on Lung Tumors," *Z. Naturforsch*, 45c:1063–1066, 1990.

Lohmann and Künzel, "Fluorescence Tomographical Studies on Breast Tissue with Cancer," *Naturwissenchaften*, 77:476–478, 1990.

Lohman, W., "Native Fluorescence of Unstained Cryo–sections of the Skin with Melanomas and Nevi," *Naturwissenschaften*, 76:442–426, 1989.

Mahadevan et al., "Optical Techniques for the Diagnosis of Cervical Precancers: A Comparison of Raman and Fluorescence Spectroscopies," *SPIE*, 2388:110–120, 1995.

Mahadevan et al., "Study of the Fluorescence Properties of Normal and Neoplastic Human Cervical Tissue," *Lasers in Surgery and Medicine*, 13:647–655, 1993.

Manoharan et al., "Ultraviolet Resonance Raman Spectroscopy for Detection of Colon Cancer," *Lasers in Life Sciences*, 6:217–227, 1995.

Manoharan et al., "Laser–induced Fluorescence Spectroscopy of Colonic Dysplasia: Prospects for Optical Histological Analysis," *SPIE*, 2388:417–421, 1995.

Montán and Strömblad, "Spectral Characterization of Brain Tumors Utilizing Laser–Induced Fluorescence," *Lasers in Life Sciences*, 1(4):275–285, 1987.

Mosier–Boss et al., "Fluorescence Rejection in Raman Spectroscopy by Shifted–Spectra, Edge Detection, and FFT Filtering Techniques," *Applied Spectroscopy*, 49(5):630–638, 1995.

Nishioka, "Laser–Induced Fluorescence Spectroscopy," *Experimental and Investigational Endoscopy*, 4(2):313–326, 1994.

Oraevsky et al., "XeCl Laser–Induced Fluorescence of Atherosclerotic Arteries. Spectral Similarities Between Lipid–Rich Lesions and Peroxidized Lipoproteins," *Circulation Research*, 72:84–90, 1993.

Ozaki et al., "Biomedical Application of Near–Infrared Fourier Transform Raman Spectroscopy, Part I: The 1064–nm Excited Raman Spectra of Blood and Met Hemoglobin," *Applied Spectroscopy*, 46(3):533–536, 1992.

Palcic et al., "Detection and Localization of Early Lung Cancer by Imaging Techniques," *Chest*, 99:742–743, 1991.

Papazoglou et al., "Laser–Induced Fluorescence Detection of Cardiovascular Atherosclerotic Deposits via Their Natural Emission and Hypocrellin (HA) Probing," *J. Photochem. Photobiol. B: Biol.*, 22:139–144, 1994.

Ramanujam et al., "In vivo Diagnosis of Cervical Intraepithelial Neoplasia Using 337–nm–Neoplasia (CIN)," *Gynecologic Oncology*, 52:31–38, 1994.

Richards–Kortum et al., "476 nm Excited Laser–Induced Fluorescence Spectroscopy of Human Coronary Arteries: Applications in Cardiology," *American Heart Journal*, 122(4)(1):1141–1150, 1991.

Richards–Kortum et al., "Spectral Diagnosis of Atherosclerosis Using and Optical Fiber Laser Catheter," *American Heart Journal*, 118(2):381–391, 1989.

Richards–Kortum et al., "A One–Layer Model of Laser–Induced Fluorescence for Diagnosis of Disease in Human Tissue: Applications to Atherosclerosis," *IEEE Transactions on Biomedical Engineering*, 36(12):1222–1232, 1989.

Richards–Kortum et al., "Survey of the UV and Visible Spectroscopic Properties of Normal and Atherosclerotic Human Artery Using Fluorescence EEMS," In *Optronic Techniques in Diagnostic and Therapeutic Medicine*, ed. R. Pratesi, Plenum, 1991, pp. 129–138.

Richards–Kortum et al., "A Model for Extraction of Diagnostic Information from Laser Induced Fluorescence Spectra of Human Artery Wall," *Spectrochimica Acta*, 45A(1):87–93, 1989.

Römer et al., "Laser–Induced Fluorescence Microscopy of Normal Colon and Dysplasia in Colonic Adenomas: Implications for Spectroscopic Diagnosis," *The American Journal of Gastroenterology*, 90(1):81–87, 1995.

Sartori et al., Autofluorescence Maps of Atherosclerotic Human Arteries–A New Technique in Medical Imaging, *IEEE Journal of Quantum Electronics*, QE–23(10):1794–1797, 1987.

Schomacker et al., "Ultraviolet Laser–Induced Fluorescence of Colonic Polyps," *Gastroenterology*, 102:115–1160, 1992.

Sterenborg et al., "In vivo Fluorescence Spectroscopy and Imaging of Human SkinTumours," *Lasers in Medical Science*, 9:191–201, 1994.

van Gemert et al., "Optical Properties of Human Blood Vessel Wall and Plaque," *Lasers in Surgery and Medicine*, 5:235–237, 1985.

Verbunt et al., "Characterization of Ultraviolet Laser–Induced Autofluorescence of Ceroid Deposits and Other Structures in Atherosclerotic Plaques as a Potential Diagnostic for Laser Angiosurgery," *American Heart Journal*, 123(1):208–216, 1992.

Yuanlong et al., "Characteristic Autofluorescence for Cancer Diagnosis and Its Origin," *Lasers in Surgery and Medicine*, 7:528–532, 1987.

Zeng et al., "Autofluorescence Distribution in Skin Tissue Revealed by Micropectrophotometer Measurements," *SPIE*, 1876:129–135, 1993.

Zeng et al., "A Computerized Autofluorescence and Diffuse Reflective Spectroanalyser System for in vivo Studies," *Phys. Med. Biol.*, 38:231–240, 1993.

International Search Report dated Nov. 24, 1997 (PCT/US97/13300) (TUUT:009P).

* cited by examiner

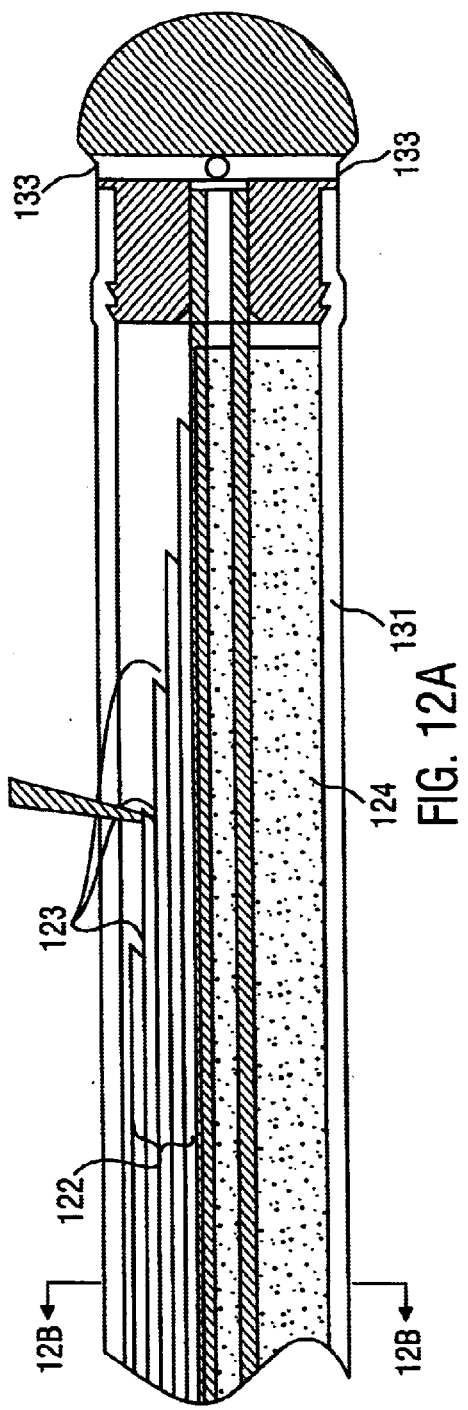
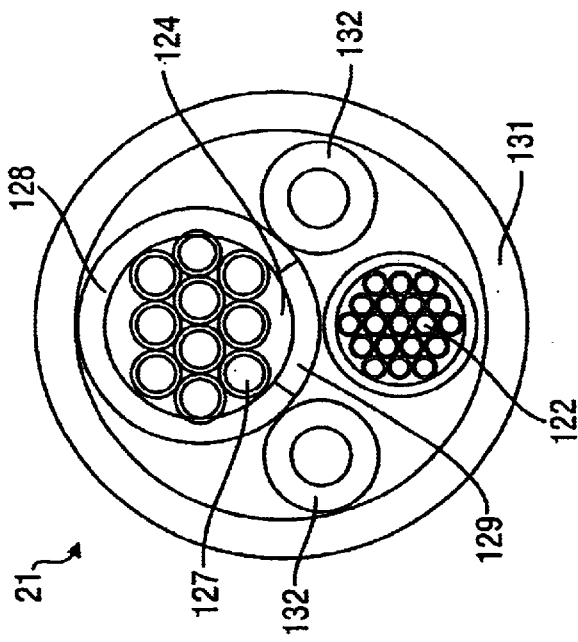
FIG. 12A
FIG. 12B

APPARATUS FOR THE CHARACTERIZATION OF TISSUE OF EPITHELIAL LINED VISCUS

This is a divisional of application Ser. No. 08/693,471, filed Jun. 22, 1999 (now abandoned).

BACKGROUND OF THE INVENTION

The present invention relates to apparatus and methods for investigating epithelial lined viscus, and more particularly to apparatus and methods for characterizing normal and dysplastic tissue of the endocervical canal.

The most prevalent of preinvasive conditions of the female lower genital tract is cervical intraepithelial neoplasia (CIN). The traditional definition calls it a spectrum of intraepithelial changes that begins as a generally well differentiated intraepithelial neoplasm, which has traditionally been classified as a very mild dysplasia, and ends with invasive carcinoma. Neoplastic changes are confined to the squamous epithelium and include nuclear pleomorphism, loss of polarity, and presence of abnormal mitoses. CIN is graded 1 to 3, based on the amount of undifferentiated cells present from the basement membrane to the surface epithelium. When one third of that distance is involved, the grade is 1; when more than one third and up to two thirds is involved, the grade is 2; when more than two thirds is involved, the grade is 3. Full-thickness involvement from the surface epithelium to the basement membrane is referred to as carcinoma in situ (CIS). The median transit time from CIN to CIS depends on the grade of CIN: for grade 1 CIN, the time is approximately 6 years; for grade 2 CIN, approximately 2 years; and for grade 3, approximately 1 year. Despite some debate in the past about CIN and CIS representing two distinct entities, it is currently believed that CIN and CIS are part of a spectrum of disease that leads to invasive cancer of the cervix. The diagnosis and treatment of CIN are thus part of the prevention of invasive cervical cancer. An accepted method to classify cervical tissues is the new Bethesda system as presented in Wright et al., "Pathology of the Female Genital Tract," 156–177, Springer-Verlag, (1994). In accordance with that system, lesions with HPV and CIN are classified as squamous intraepithelial lesions (SILs) where they may be further separated as high grade SIL (CIN II, CIN III, CIS) and low grade SIL (CIN I, HPV). Normal, metaplastic and non-specific inflammation tissues are classified as non-SILs.

Cervical intraepithelial neoplasia is usually detected by screening Pap smears from asymptomatic women. Patients with abnormal Pap smears are referred for colposcopy and possibly biopsy. Acetic acid is applied to the cervix, and areas with abnormal DNA content, such as those with CIN, turn white. The colposcope, a mounted magnifying lens, is used to direct biopsies of the abnormal white areas. Abnormal configurations of blood vessels, called vascular atypia, signal disordered growth and help the clinician know which other areas require biopsy. An appropriate evaluation of the abnormal Pap smear involves review of the referral and repeat Pap smears, endocervical curettage, and multiple biopsies of the aceto white areas; the results of such analysis will indicate whether the patient has CIN.

While the predictive accuracy of colposcopy is a matter of debate in the field with some researchers finding excellent overall accuracy with others finding accuracy to be poor for CIN but good for condyloma.

Recently, there has been intensive research to explore the use of optical spectroscopy for the diagnosis of disease in human tissue. Several studies have successfully demonstrated the use of fluorescence, infrared absorption and Raman spectroscopies for disease diagnosis in various organ systems. Auto and dye induced fluorescence have shown promise in recognizing atherosclerosis and various types of cancers. Many groups have utilized autofluorescence for differentiation of normal and abnormal tissues from the human breast and lung, urinary bladder and gastrointestinal tract.

Copending application Ser. No. 08/666,021, filed Jul. 19, 1996, assigned to the same assignee as the present application, discloses a system that uses fluorescence spectroscopy to discriminate diseased (pre-cancerous and cancerous) from non diseased (normal tissues and inflammation) tissue as well as differentiate cancer and high grade pre-cancers from low grade precancerous lesions of the human cervix in vivo. This system provides more effective patient management, as 1) fluorescence measurements, and hence diagnostic information, can be obtained in real time and 2) the technique is non-invasive. In vitro studies in which fluorescence was measured from cervical biopsies over the UV and visible regions of the spectrum have shown that the fluorescence intensity of histologically abnormal cervix is significantly lower than that of the normal cervix from the same patient. In accordance with the above-referenced copending application, the system includes a fiber optic probe, illumination source and optical multi channel analyzer. The probe is inserted through the vaginal canal until its tip is flush with the surface of the cervix. The probe delivers light at specific excitation wavelengths and collects fluorescence from the entire emission wavelength range from a predetermined area of the cervix. During colposcopy, spectra are collected from each colposcopically abnormal area of the cervix prior to biopsy and from 1 to 4 colposcopically normal areas. Using this system, laser induced fluorescence acquired from human cervical tissues in vivo at 337, 380 and 460 nm excitation is analyzed to identify cervical intraepithelial neoplasia (CIN).

A limitation of previous colposcopic and fluorescence spectroscopic systems is that they are not capable of sampling the endocervix. It is known that atypical colposcopic tissue patterns occur with some frequency at the transformation zone between the squamous and columnar epithelium in the endocervical canal. See, Burke L, Antonioli D A and Ducatman B S. *Colposcopy, Text and Atlas,* pp. 47, 48, 61 and 62, Appleton and Large, Norwalk Conn. (1991) This transformation zone (also known as the squamocolumnar junction) is often located well within the endocervical canal and is not easily subjected to colposcopy or fluorescence spectroscopy using existing systems which are intended primarily to assess the ectocervix. In addition, cervical lesions that exist on the ectocervix often extend into the endocervical canal, and characterization of the lesion within the endocervical canal is often an important matter.

It would therefore be desirable to provide a means to subject the endocervical canal, including the transformation zone, to fluorescence spectroscopy.

SUMMARY OF THE INVENTION

The present invention avoids the above noted drawbacks of the prior art by providing a method and apparatus for characterizing tissue of epithelial lined viscus including, for example, the endocervical canal. In particular, in accordance with a method embodying the present invention, endocervical canal tissue is characterized in vivo, by illuminating endocervical canal tissue in vivo with electromagnetic radiation wavelengths to produce a plurality of fluorescence intensity spectra, detecting a plurality of emission wavelengths from the fluorescence intensity spectra, and characterizing the endocervical canal tissue as a function of the emission wavelengths. The characterizing step may distinguish squamous epithelium and columnar epithelium tissue, normal squamous and abnormal tissue, normal columnar epithelium and abnormal tissue, inflamed and abnormal tissue, low grade SIL and high grade SIL tissue, or normal and high grade SIL tissue.

In addition, the illuminating and detecting steps may comprise, illuminating a substantially cylindrical area of the endocervical canal tissue, and detecting the plurality of emission wavelengths from selected portions of the cylindrical area. The illuminating and detecting steps may further comprise illuminating an area of the endocervical canal in a vicinity of a single pixel, and detecting the plurality of emission wavelengths from the single pixel, and repeating the illuminating and detecting steps to substantially cover the cylindrical surface. In another embodiment, the illuminating and detecting steps may further comprise illuminating a substantially ring-shaped area of the endocervical canal, detecting the plurality of emission wavelengths from the substantially ring-shaped area, and repeating the illuminating and detecting steps to substantially cover the cylindrical surface. In yet another embodiment, the illuminating and detecting steps may further comprise, illuminating a substantially line-shaped area of the endocervical canal, detecting the plurality of emission wavelengths from the substantially line-shaped area, and repeating the illuminating and detecting steps to substantially cover the cylindrical surface.

In addition, the electromagnetic radiation wavelengths used to practice the method of the present invention may be in the ranges of 317–357 nm, 360–400 nm and 440–480 nm.

In addition, an apparatus embodying the present invention for characterizing endocervical tissue, comprises, a light source for emitting a plurality of electromagnetic radiation wavelengths; a probe connected to the light source, the probe adapted to apply the plurality of electromagnetic radiation wavelengths to an interior surface of endocervical canal tissue under test and to gather fluorescence emitted from the tissue under test; a detector, connected to the probe, for detecting at least one fluorescence spectrum emitted from the tissue under test, and a programmed computer connected to the detector means, for processing the at least one fluorescence spectrum according to a predetermined algorithm to characterize the tissue under test.

The light source may be a laser light source or a filtered white light source and the plurality of electromagnetic radiation wavelengths may be about 337 nm, about 380 nm and about 460 nm. The probe may include excitation optical fibers for applying the plurality of electromagnetic wavelengths to an interior surface of the endocervical tissue under test, and collection optical fibers for gathering the fluorescence emitted from the endocervical tissue under test.

These and other features and advantages of the present invention will become apparent to those of ordinary skill in this art with reference to the following detailed description.

BRIEF DESCRIPTION OF THE DRAWINGS

FIGS. 12A and 12B are an exemplary embodiment of a line probe useable in the present invention.

DETAILED DESCRIPTION

Measurement Apparatus

Figure 1:
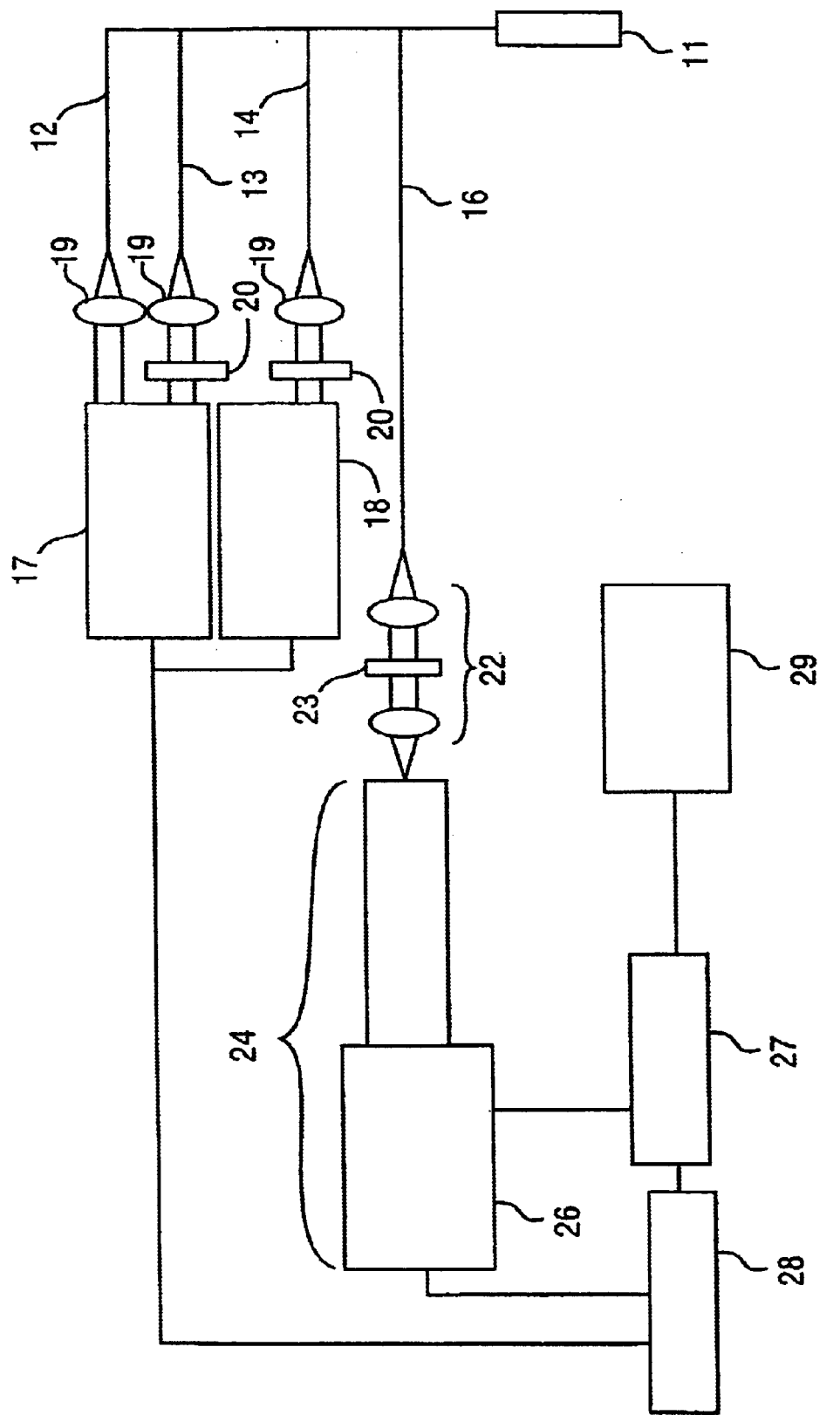
FIG. 1 is an exemplary apparatus in accordance with the present invention usable to perform the method of the present invention.
Figure 2:
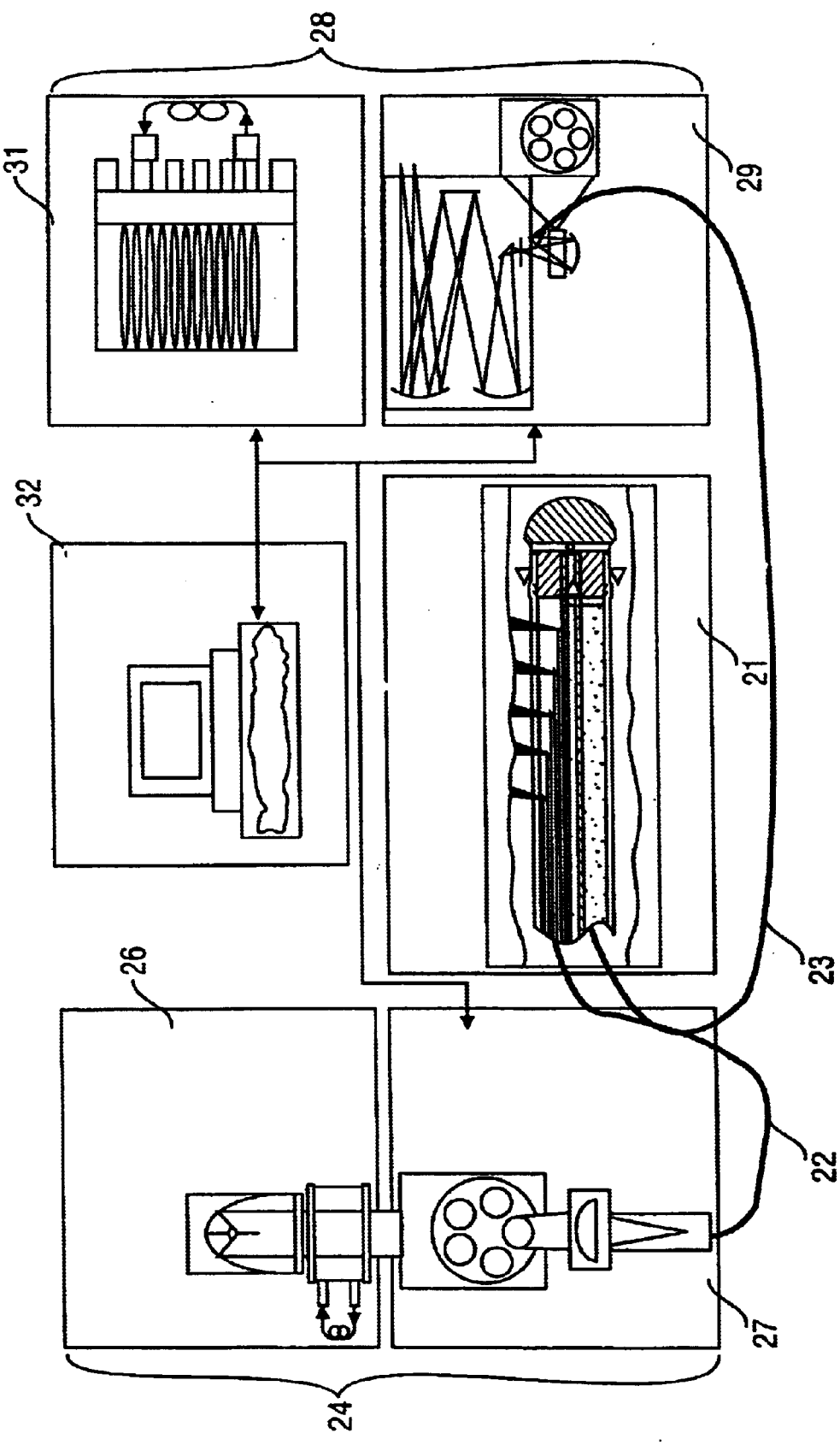
FIG. 2 is another exemplary apparatus in accordance with the present invention usable to perform the method of the present invention.

FIGS. 1 and 2 present exemplary embodiments of the apparatus of the present invention which are useable to practice the method of the present invention.

Referring first to FIG. 1, an apparatus is disclosed using a single pixel optical probe. Exemplary embodiments of the single pixel probe are presented in more detail below with reference to FIGS. 4 and 5. The apparatus includes endocervical probe 11 which, as described below in more detail, incorporates a number of optical fibers including excitation fibers 12, 13 and 14 and collection fiber 16. The excitation fibers are connected to an illumination source which may be, for example, two nitrogen lasers 17,18 (LN300C, Laser Photonics) with a dye module. Other illumination sources, for example a Xenon lamp and filter wheel (disclosed in more detail with reference to FIG. 2), may also be used. Other illumination sources may also be acceptable, including, for example, various types of lasers (for example, HeCd or Ag lasers) used with or without dye modules, and various types of so-called-white light sources (for example, Xe, Hg, or XeHg lamps) used with filter wheels. This illumination source produces light at frequencies that have been selected for their ability to produce fluorescence in tissue that permits characterization of the tissue, For example light at approximately 337, 380 and 460 nanometers has proven useful. This light is coupled into excitation fibers 12, 13, 14. For coupling, standard Microbench components (Spindler Hoyer) and planoconvex lenses 19 were used. The light coming out of the two dye modules is bandpass filtered by bandpass filters 21 to minimize fluorescence from the dye being coupled into the excitation fibers 12, 13 and 14. Collection fiber 16 collects the fluorescence which is projected through a coupling optics 22 (for example, Microbench, magnification 50/30) into a detector 24, for example an F/3.8 spectrograph (Monospec 18, Thermo Jarrel Ash, Scientific Measurement Systems, Inc.). In the coupling optics 22, longpass filter 23 (for example, color glass filters, Schott) block the reflected excitation light from entering the detector. The spectrograph disperses the light onto an intensified diode array 26. Exemplary diode array 26, electronics and controller 27 are manufactured by Princeton Instruments. The system also includes gate pulser 28 which is used to control the operation of lasers 17 and 18. Lasers 17 and 18 may be controlled, for example at a 30 Hz repetition rate with a 5 nanosecond pulse duration, but other repetition rates and pulse durations may also be acceptable.

The apparatus also includes programmed computer 29 which operates to energize lasers 17 and 18 and to analyze the fluorescence spectra collected by collection fiber 16 in order to characterize the tissue sample under study. Details of this control and analysis may be found in copending application Ser. No. 08/666,021, filed Jul. 19, 1996, the disclosure of which is incorporated herein by reference.

Referring now to FIG. 2, an apparatus embodying the present invention is disclosed using a multiple pixel optical probe. Exemplary embodiments of multiple pixel optical probes are presented in more detail below with reference to FIGS. 6–12. The apparatus includes a multiple pixel optical probe 21 which incorporates excitation optical fibers 22 and collection optical fibers 23. Excitation optical fibers 22 are connected to receive light from illumination source 24 which may be, for example, a Xenon lamp 26 in combination with a filter wheel 27. Once again, other illumination sources, including for example, the laser source disclosed with reference to FIG. 1, would also be acceptable. As with the apparatus of FIG. 1, illumination source 24 produces light at frequencies that have been selected for their ability to produce fluorescence in tissue that permits characterization of the tissue.

Collection fibers 23 from probe 21 are connected to detector 28 which includes, for example, an imaging spectrograph 29 (for example, a Chromex 250 IS), and a CCD array 31 (for example, a thermoelectric cooled CCD Princeton Instruments EV 578x384). The output of detector 28 is applied to computer 32 which is programmed to control illumination source 24 and to analyze the fluorescence spectra collected by collection fibers 23 and detected by detector 28 using, for example, the analysis methods disclosed in the aforementioned copending application.

Endocervical Canal Morphology

Figure 3A:
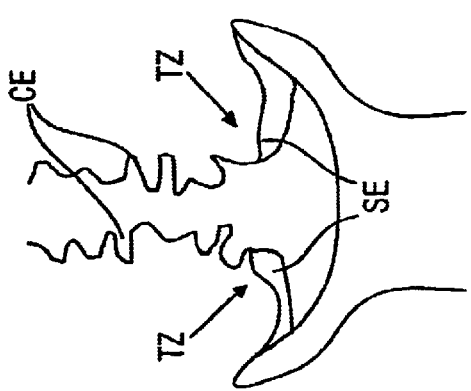
FIGS. 3A–3E illustrate various states of the endocervical canal.
Figure 3D:
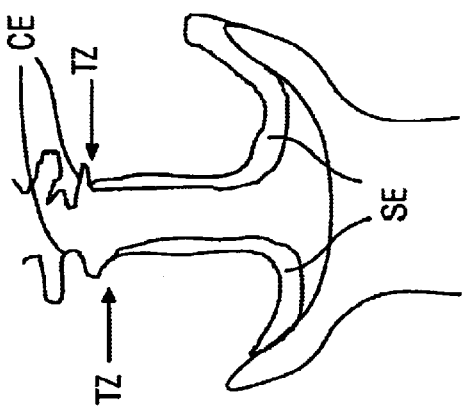
Figure 3B:
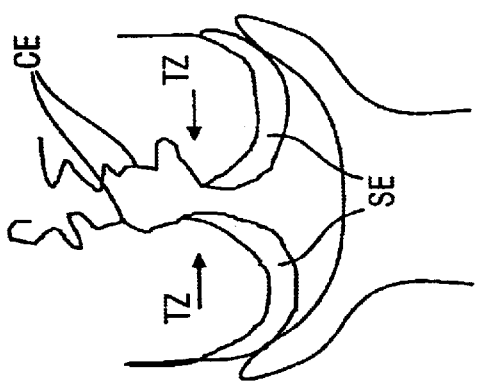
Figure 3E:
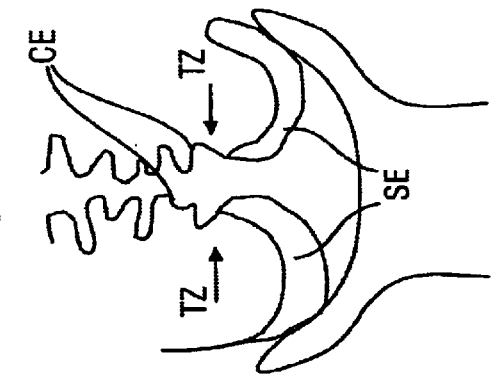
Figure 3C:
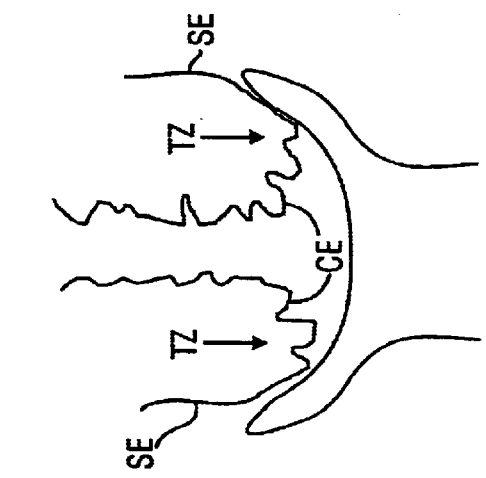
Figure 3F:
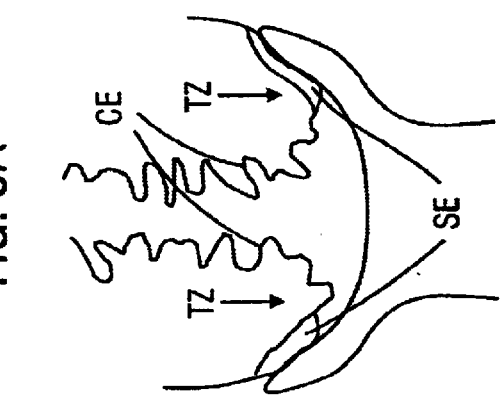

Referring now to FIGS. 3A–F, shown are simplified representations of the cross section of the os of the endocervical canal and surrounding tissue illustrating the locations of the squamous epithelium (SE), columnar epithelium (CE) and transformation zone (TZ) of the uterus at various stages of maturity and for various medical conditions. Specifically, FIG. 3A shows the neonate uterus, FIG. 3B shows the premenarchal uterus, FIG. 3C shows the menarchal uterus, FIG. 3D shows the menstruating uterus, FIG. 3E shows the menopausal uterus and FIG. 3F shows the postmenopausal uterus. As can be seen, the transformation zone TZ can appear on the ectocervix (for example, menstruating, FIG. 3D), or well within the edocervical canal (for example, postmenopausal, FIG. 3F), or anywhere in between. Since the most common location for CIN and metaplasia is at or near the transformation zone, it is critical that the transformation zone be imaged when conducting fluorescence spectroscopy. This is of particular importance in menopause and postmenopause because most cervical carcinomas occur at this age, and this is when the transformation zone is most deeply within the endocervical canal.

Other general observations of the morphology of the endocervical canal are worthy of note. After the external os, which follows a funnel type opening, the endocervical canal enlarges and gets smaller again at the inner os. The uterus opens to its full size after the internal os by a small angle. The canal can be filled inside with non-neoplastic additional tissue like polyps and synechia. Polyps may fill the canal. Atrophy may be present, which results in an abnormal form of the wall (missing folds). In addition, It is known that stenosis may occur after LEEP treatments.

The folds of the columnar epithelium may typically be several centimeters deep with varying shapes. For example, in one uterus that was studied after removal by hysterectomy, the folds were a maximum of 7.83 mm with a mean depth of 3.38 mm. The folds were observed to have two main directions: axial and with an angle of approximately 30 degrees to the axis of the canal. The top of this pine tree-like form points outwards the canal. The folds are filled with mucus that sticks strongly to the tissue. Flushing with saline solution will not remove the mucus. A study of the fluorescence characteristics of cervical mucus are presented below with reference to FIGS. 14 and 15.

Optical Probes

Figure 4A:
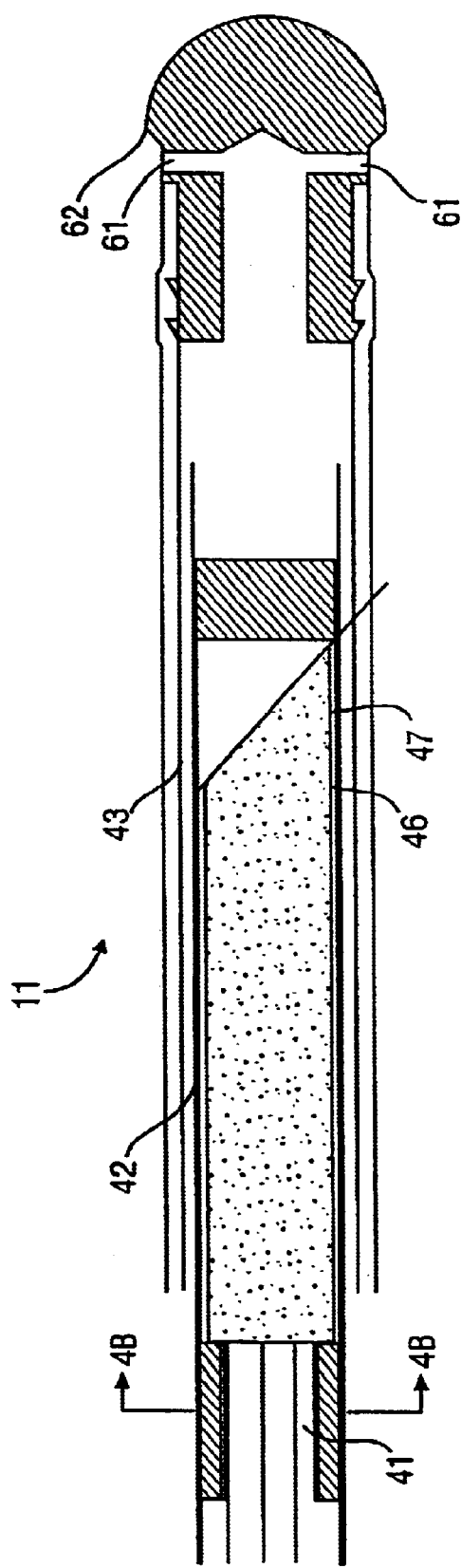
FIGS. 4A and 4B are an exemplary single pixel probe usable in the present invention.
Figure 4B:
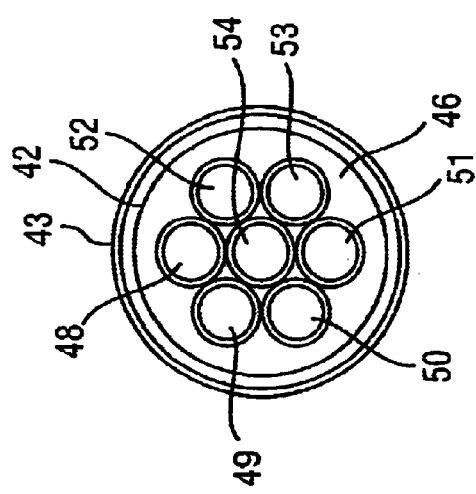

FIGS. 4A and 4B are a single pixel probe 11 that may be used in the apparatus of FIG. 1 in accordance with the present invention. Referring to FIG. 4A, optical probe 11 includes a bundle of optical fibers 41 which are packed in a fluorinated ethylene-propylene (FEP) tubing 42 that is substantially transparent to visible light and that also transmits in the ultraviolet. The FEP tubing 42 containing the fibers 41 is flexibly mounted within a second tubing 43 which may also be made of FEP. The outer diameter of tubing 43 is preferably less than 2 mm, however other dimensions may be used. The outer diameter of tube 43 is determined primarily by anatomical constraints of the endocervical canal, and is discussed in more detail below with reference to FIG. 13. This dimension allows the passage of the probe through an endocervical canal with a stenosis at the outer os. The fiber 41 within tubing 42 may be rotated and axially displaced within tubing 43 in order to permit the testing of several tissue sites without moving tubing 43.

Although FEP has proven useful for use as the material for the tubings used in the optical probes of the present invention, other materials may also be acceptable, including, for example, other plastics such as polytetrafluorethylen (PTFE), glass and quartz.

In the embodiment of FIGS. 4A and B, a short piece of a large diameter fiber 45 is used. as a reflector and the end surface 47 of fiber 45 is polished with an oblique angle (for example, 40°) relative to the axis of probe 11. Reflection of light emitted by fibers 41 toward the tissue sample under study (downward in FIG. 4A) and reflection of light emitted by the tissue sample back toward fibers 41 occurs because of total internal reflection. An alternative reflector may be made using an angled mirrored surface of polished metal, glass, sapphire, or the like.

FIG. 4B is a cross section through section 4B—4B of FIG. 4A, and shows the configuration of fibers 41. In the exemplary embodiment there are seven fibers 41, six illumination fibers 48–53, and one collection fiber 54, however any number of fibers may be used. In the exemplary embodiment, illumination fibers 48 and 51 are used for 337 nm, fibers 49 and 52 are used for 380 nm and fibers 50 and 53 are used for 460 nm. and collection fiber 54 provides a single pixel collection for fluorescence spectroscopy. It should be noted that any combination of illumination and collection fibers may be used without departing from the scope of the invention. For example, three illumination fibers and one collection fiber may be used, three illumination fibers and three collection fibers may be used., one illumination fiber and one collection fiber may be used, one fiber used for the combined purpose of illumination and collection may be used, and so forth. Fibers 48–54 may be, for example, type SFS320/385T optical fibers, and fiber 46 may be a type SFS1500/1650N optical fiber, both available from Fiberguide Industries, however other types may also be used. The single pixel embodiment results in a single substantially elliptical measurement and illumination spot, or pixel.

The part of probe 11 that extends outside the vagina preferably has a rigid tube with markings which may be used as an aid in positioning the probe both axially and rotationally. Saline solution may be flushed though the openings 61 in tip 62 of probe 11 before or during a testing procedure.

Figure 5:
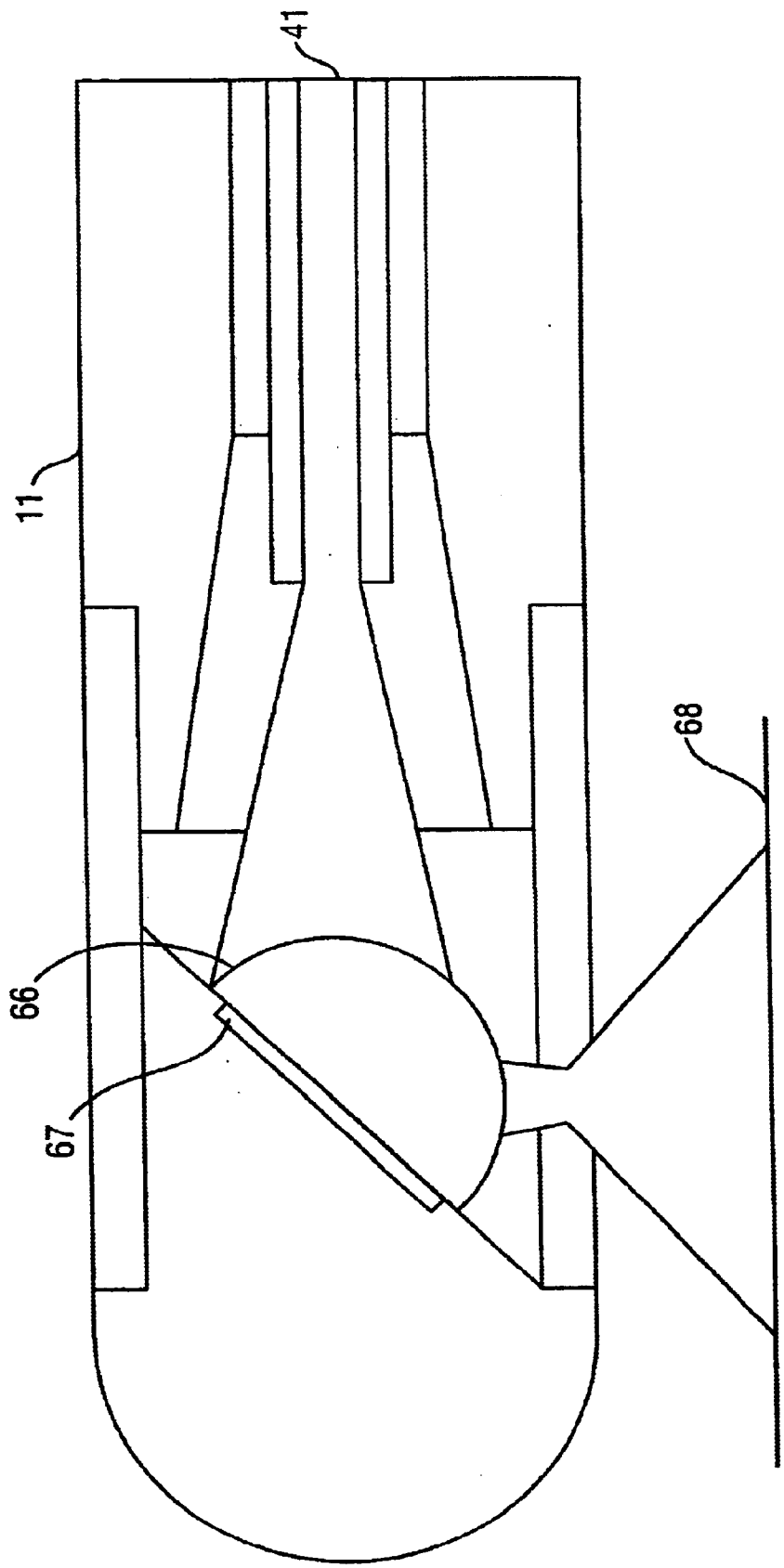
FIG. 5 is another exemplary embodiment of a single pixel probe usable with the present invention.

FIG. 5 is an alternative embodiment of the single-pixel probe of the present invention. Referring to FIG. 5, probe 11 includes fiber bundle 41 like that of the embodiment of FIG. 4A. light emitted from the end of fibers 41 is focused by lens 66 and reflected by reflecting surface 67 toward a tissue sample 68 under study. Similarly, light emitted by a tissue sample 68 is focused by lens 66, and reflected by reflective surface 67 back toward fibers 41. Other structural details remain substantially as in FIG. 4A.

Figure 7:
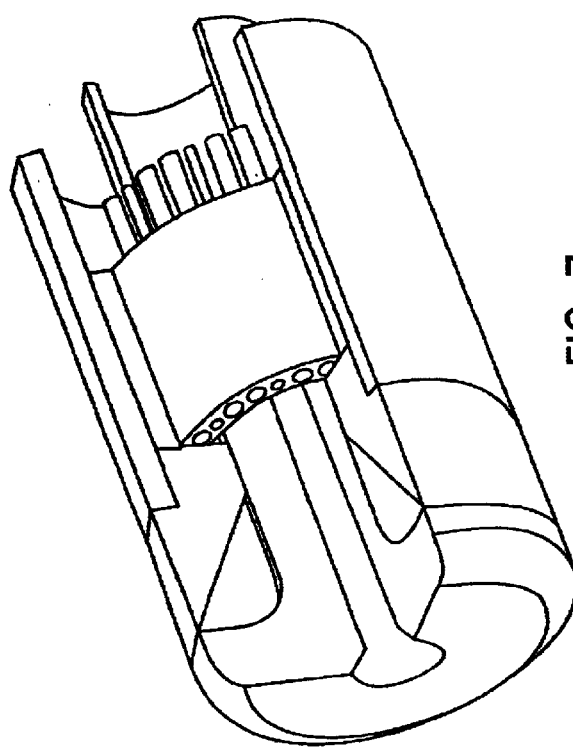
FIGS. 6–11 are various exemplary embodiments of a ring probe useable in the present invention.
Figure 6:
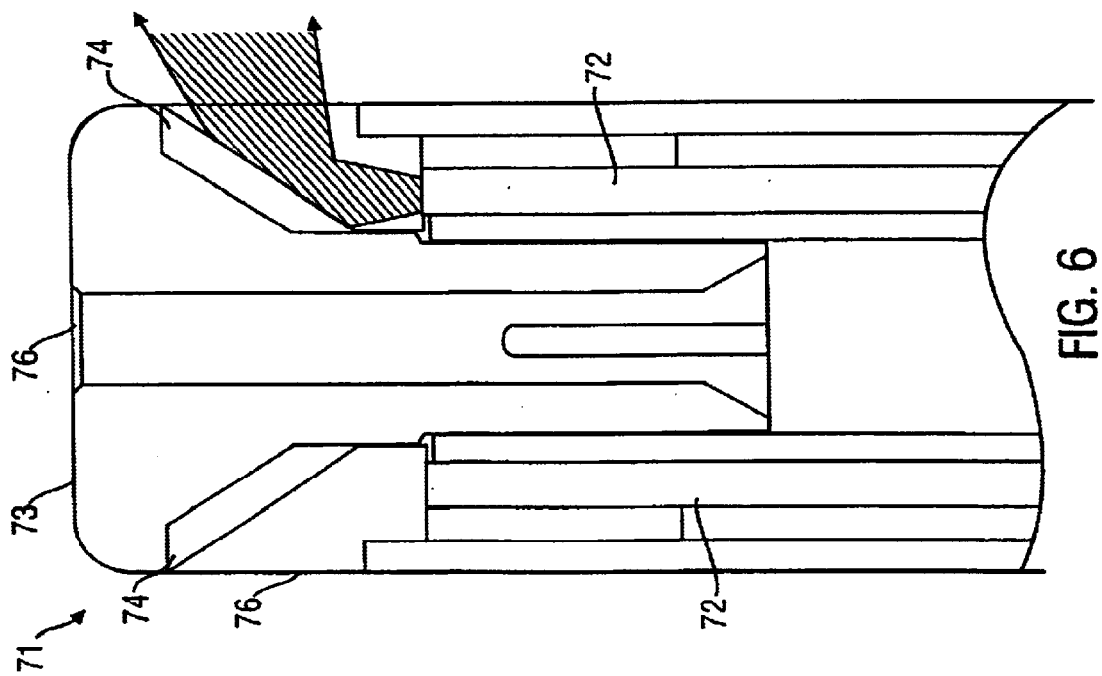
Figure 9:
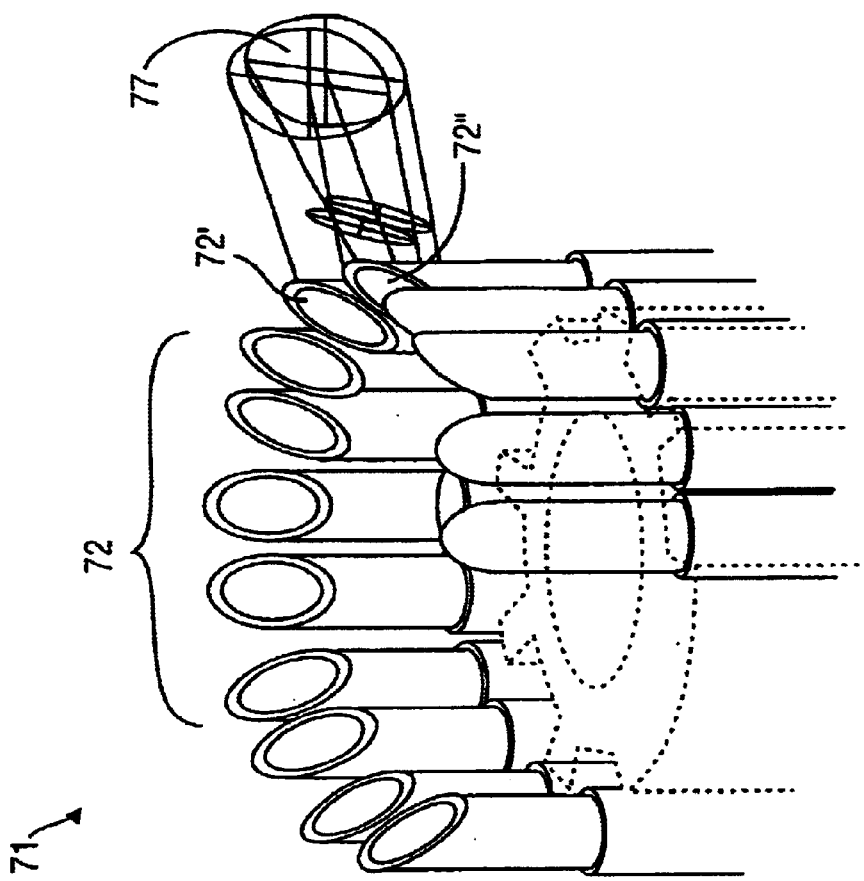
Figure 8:
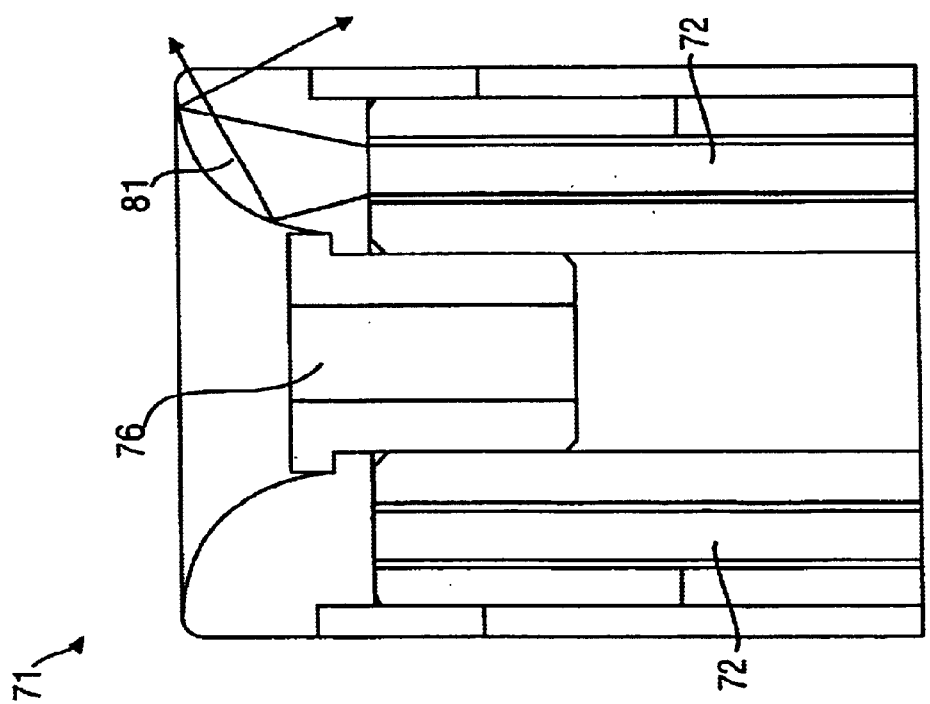
Figure 11:
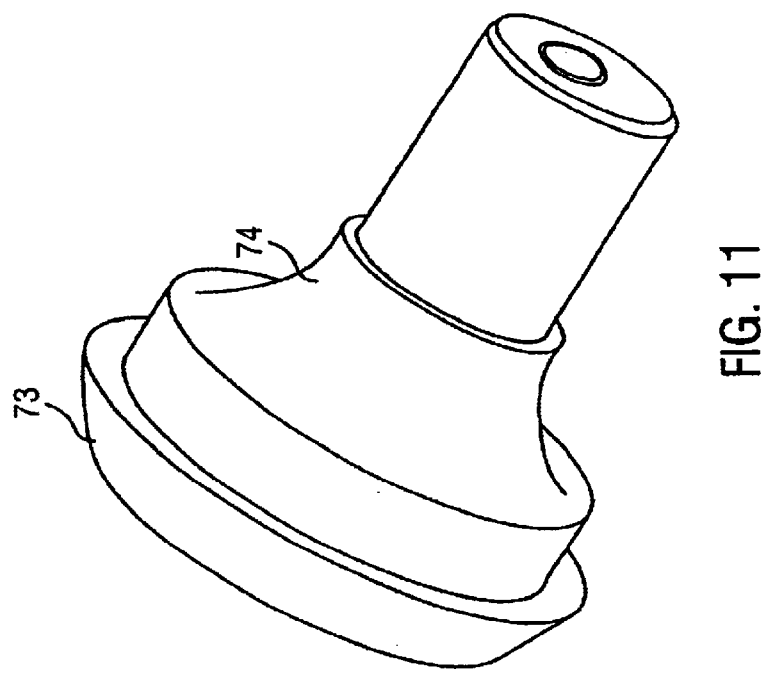
Figure 10:
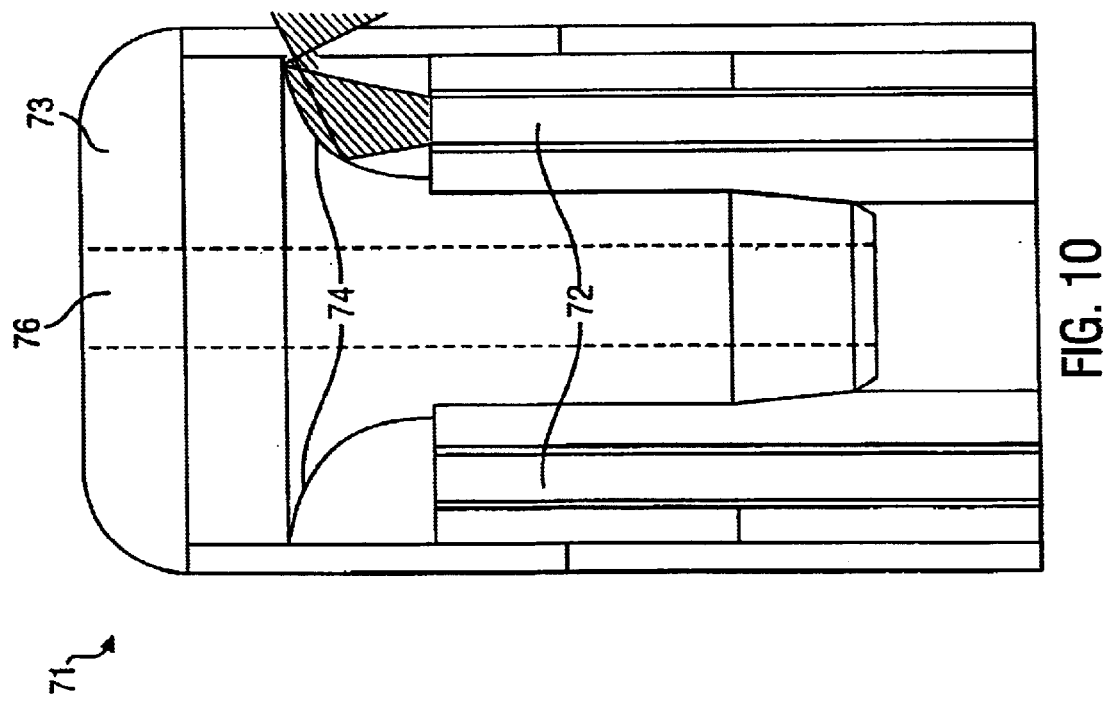

Referring now to FIGS. 6 and 7, a ring optical probe 21 is disclosed that may be used in the apparatus of FIG. 2 Probe 21 includes a number of optical fibers 72 coaxially arranged in a ring shape. In one embodiment every other one of fibers 72 are used for illumination, with the remaining fibers being used for collection. Alternatively, each fiber 72 may be used for both illumination and collection. In the embodiment of FIGS. 10 and 11, reflection of both illuminating light and collected light is done by a metal plug 73 with a polished reflecting surface 74 Alternately, a sapphire tip 81 may be used as shown in FIG. 8. In yet another embodiment, the ends of fibers 72 may be cleaved and polished as shown in FIG. 9. In the embodiment of FIG. 9, every other fiber may be used as an illumination fiber with all remaining fibers being collection fibers. This would result in adjacent fibers (for example, fibers 72' and 72") acting together to illuminate and detect from a single tissue area 77. Alternately, each of fibers 72 may have the combined function of illumination and collection. It should be noted that for the sake of clarity, the surrounding tube is not shown in the embodiment of FIG. 9.

In all embodiments of the ring probe 21, light is reflected from fibers 72 toward a tissue sample located adjacent the exterior wall of probe 21 and light emitted by the tissue sample is reflected back toward fibers 72. This results in a plurality of substantially elliptical measurement and illumination spots, or pixels distributed in a ring shape.

In the ring probe 21 embodiment of FIGS. 6, 7 and 8, channel 76 may be included to permit the flushing of the tissue under test with saline either before or during a test . . . The diameter of probe 21 may be, for example, approximately 2.8 mm, however other diameters may also work.

Referring now to FIGS. 12A and 12B disclosed is yet another embodiment of optical probe 21 usable in the apparatus of FIG. 2. The optical probe 21 of FIGS. 12A and 12B is a line probe. The probe 21 includes of an illuminator that serves to illuminate a tissue sample under study, and a collector that serves to collect light emitted by the tissue sample under study. The collector in the exemplary embodiment is made of 19 100 micrometer optical fibers 122 (type SFS100/110T available from Fiberguide Industries), however, any number of optical fibers may be used. In the disclosed embodiment, The collection of the fluorescence occurs every 1.5 mm with one of the collection fibers 122. The collection fibers 122 are polished at an oblique angle relative to the longitudinal axis of the fiber 122 (for example, 40°). The ends 123 of the collection fibers 122 are positioned at different axial locations along the probe as shown in FIG. 12A. In the exemplary embodiment this results in a simultaneous collection every 1.5 mm along a line approximately 2.5 cm. long. The diameter of the line probe 21 of FIG. 12A is approximately 3 mm, however other diameters would also be acceptable The illuminator of probe 21 in FIG. 12A includes a diffuser 124. Diffuser 124 is mounted on the top of a bundle of fibers 127. Fibers 127 may be for example type SFS200 200 micrometer optical fibers available from Fiberguide Industries, however other types of fibers may be acceptable. A reflective coating 128 over 270 degrees of diffuser 124 allows a directed illumination over approximately 90 degrees of the circumference. of probe 21. The diffuser 124 is available, for example, from Rare Earth Medical.

The diffuser 124 is packed in a FEP tubing 131 that is substantially transparent in the visible and also in the ultraviolet. Included within tubing 131 is the collection bundle 122, the diffuser 124 and flushing channels 132 used to carry saline to ports 133 in probe 21 thus permitting flushing of the tissue either before or during testing. The outer diameter of tubing 131 is preferably less than 3 mm, however, other diameters may also be acceptable. This allows the passage of the probe through most endocervical canals.

The probe is manually placed into the endocervical canal. Because of its stiffness the whole probe can be pressed against the walls of the endocervical canal while still keeping a minimal bendability.

Because 100 micron fibers 122 are used for collection the size of each measured spot or pixel in the exemplary embodiment of FIG. 12A will be smaller than approximately 0.5 mm. The diameter depends on the distance of the collection fiber 122 to the tissue. This distance may not be constant for all fibers and typically varies from approximately 0.3 to 1 mm.

The illumination light passes perpendicular through the collection fibers 122. Therefore the jacket of these fibers 122 should be removed. Collection fibers 122 will then act as cylindrical lenses.

Figure 13:
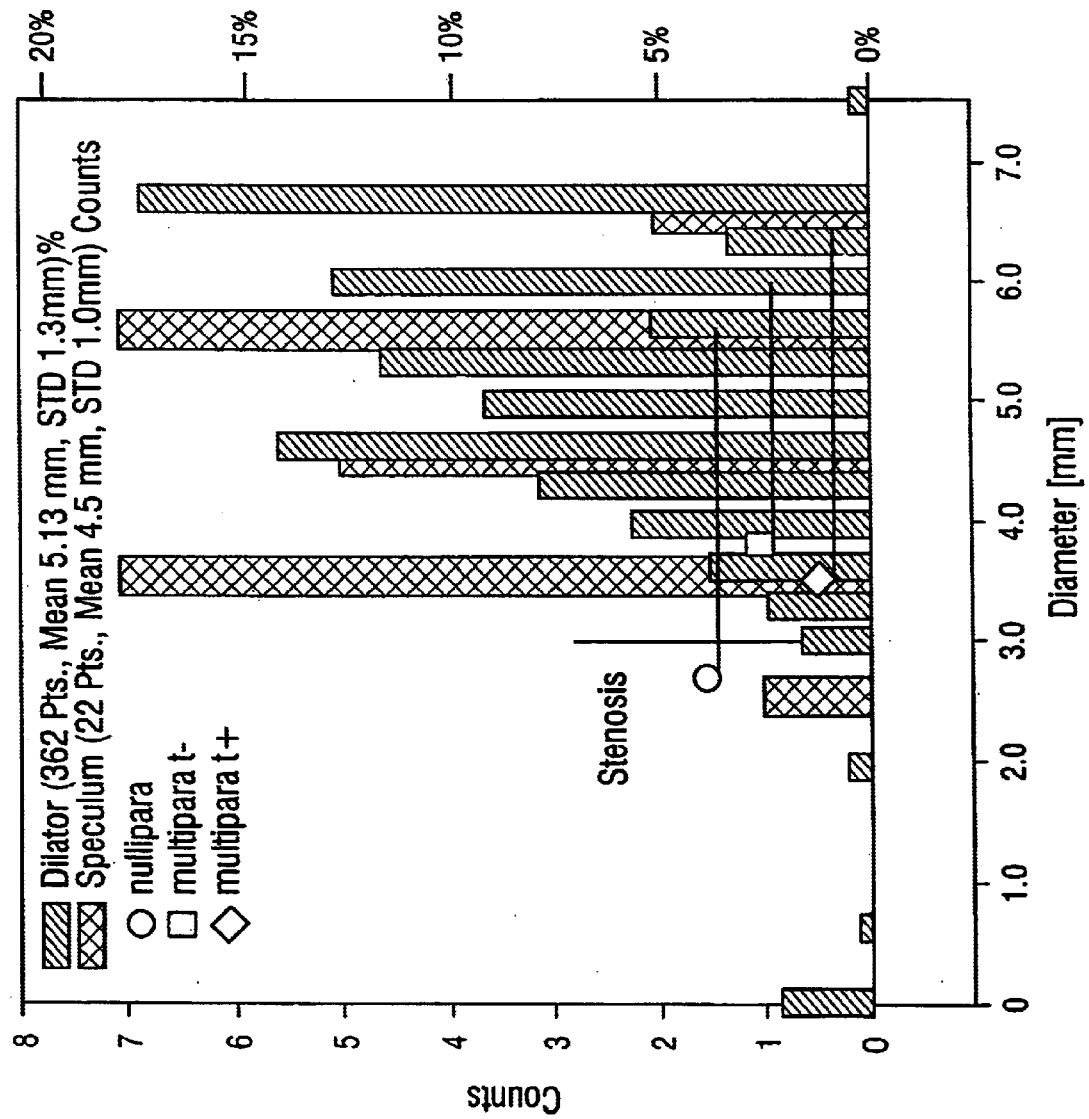
FIG. 13 is a graphical representation of a study of endocervical canal size.

Referring now to FIG. 13, presented in graphical form are the results of a study of cervical size. Because the design of the probe used in the present invention depends on the canal properties the geometrical aspects of the endocervical canal were studied. A database of 362 patients at the MD Anderson Cancer Center contained measurements of the diameter of the external os. The obtained diameter is based on the size of a dilator used at MD Anderson to measure the endocervical canal prior a LEEP or LEEP cone treatment. In a following checkup visit the canal is checked again to assure no stenosis occurred. This parameter was measured in another series of 22 patients with similar results.

From FIG. 13 it can be seen that the endocervical canal has a mean diameter at the outer os of 5 mm. In most patients the outer os is larger than 3 mm and smaller than 7 mm. The length of the canal was estimated from a uterus removed by hysterectomy. The endocervical canal was measured to be approximately 4 cm long. These mechanical dimensions may then be considered in determining a size of the optical probes used in the present invention. For example, the study reflected in the graph of FIG. 13 indicates that the optical probe should preferably be less than 3 mm in diameter if a single sized probe is to be used for all patients. Of course, probes of different sizes may also be used.

Figure 14:
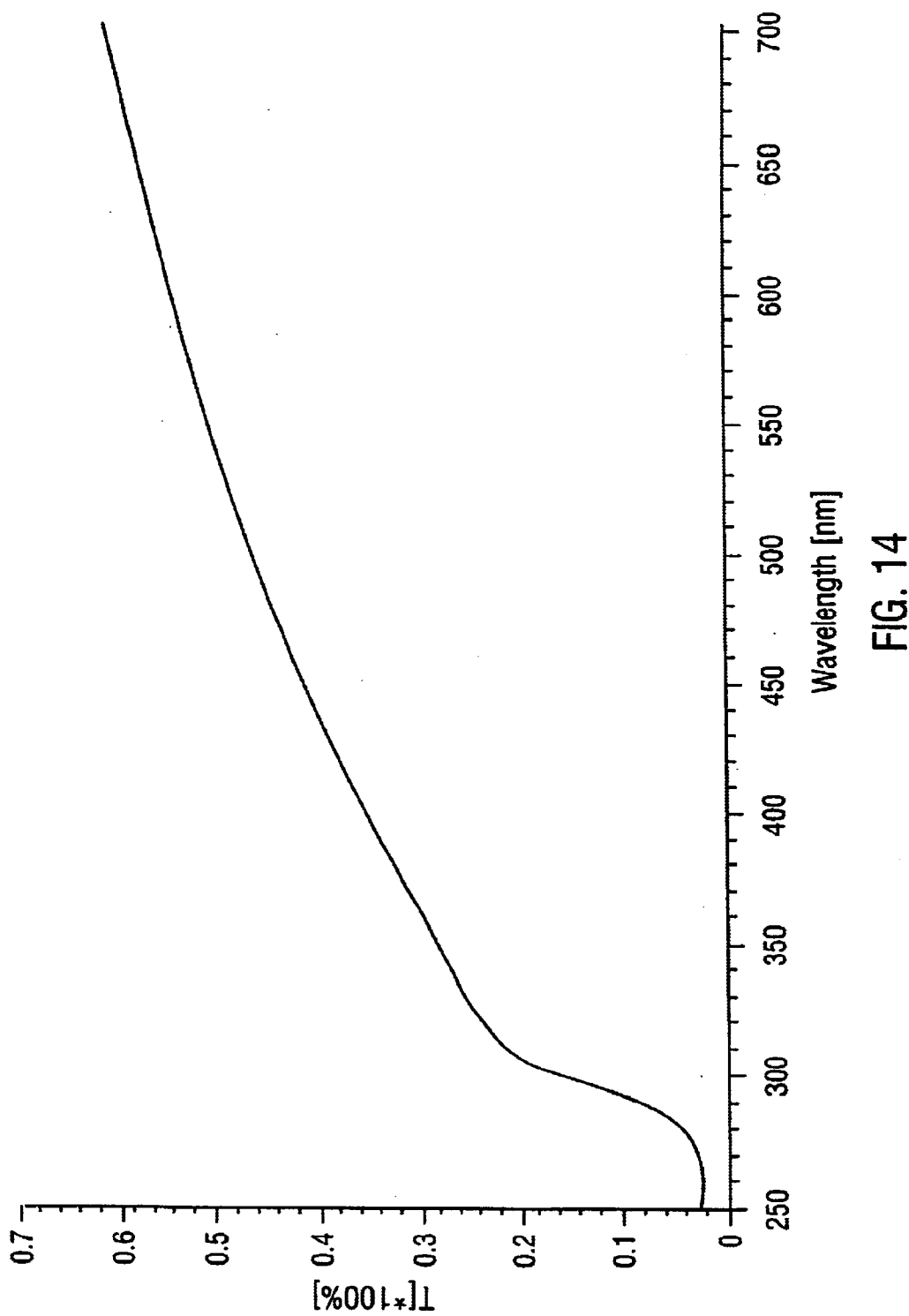
FIGS. 14 and 15 are graphs showing the optical transmission and excitation emission of cervical mucus.
Figure 15:
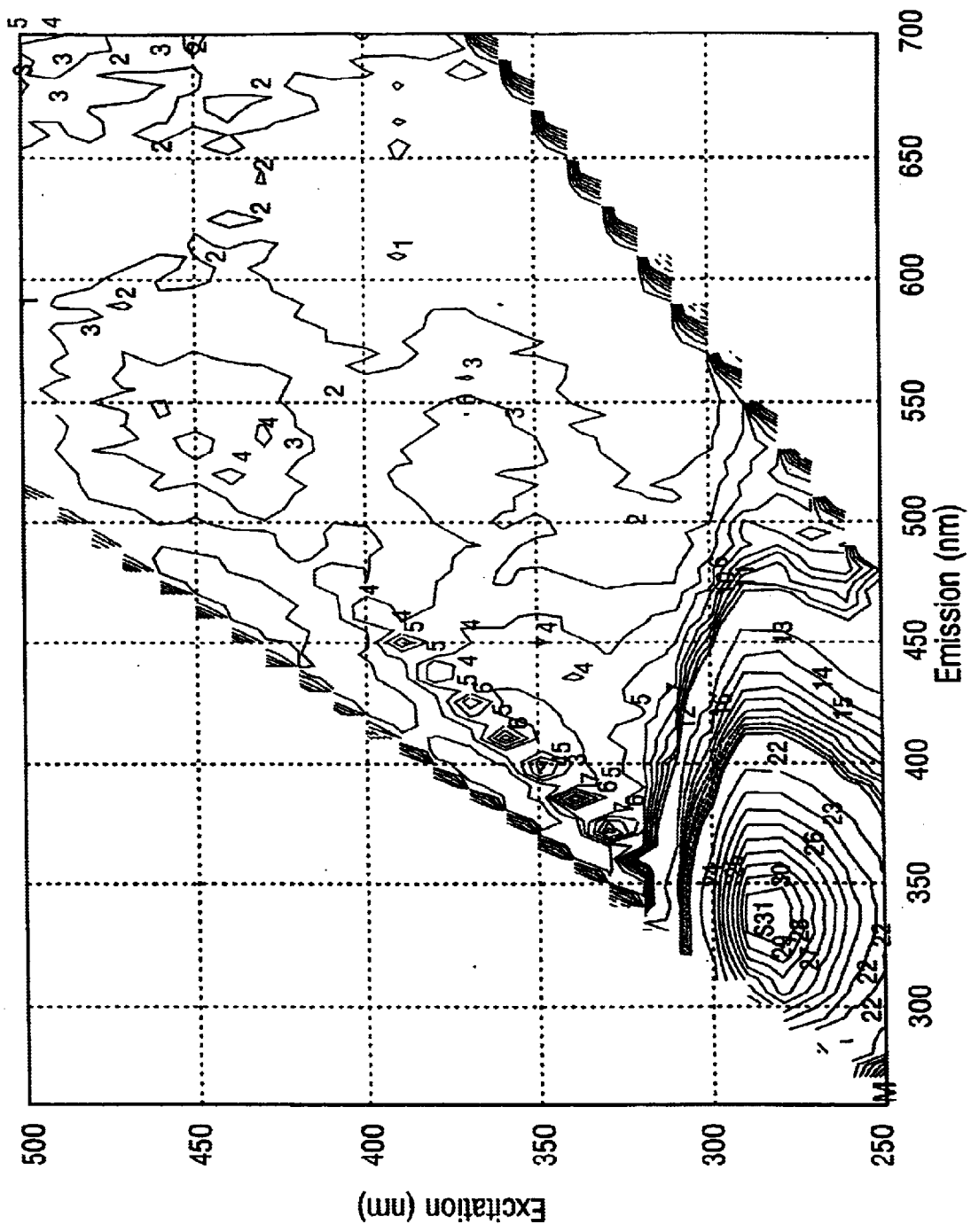

In addition, in order to determine the possible effects of mucus in the endocervical canal, the transmission and fluorescence of several samples of mucus was measured, and the results are presented in graphical form in FIGS. 14 and 15. To produce these graphs, small amounts of mucus were diluted in 10 ml of normal buffered saline solution and placed in a 1 cm pathlength.

As can be seen with reference to FIGS. 14 and 15, the strongest emission of mucus is at 340 nm emission with an excitation at 280 nm. This will not interfere with the measurements performed by the disclosed exemplary embodiments of the present invention.

Figure 16:
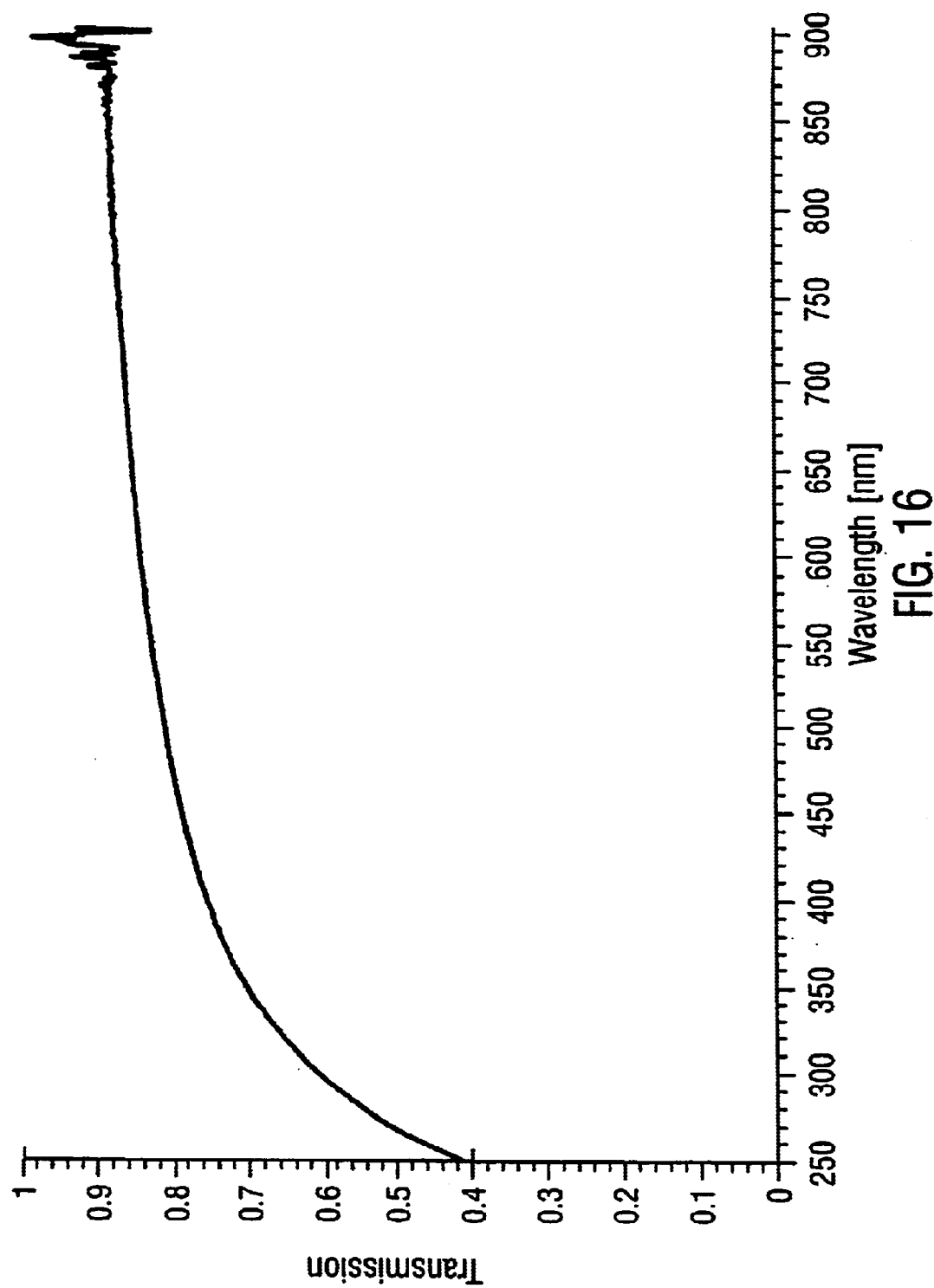
FIGS. 16 and 17 are graphs showing the optical transmission and excitation emission of fluorinated ethylene-propylene (FEP).
Figure 17:
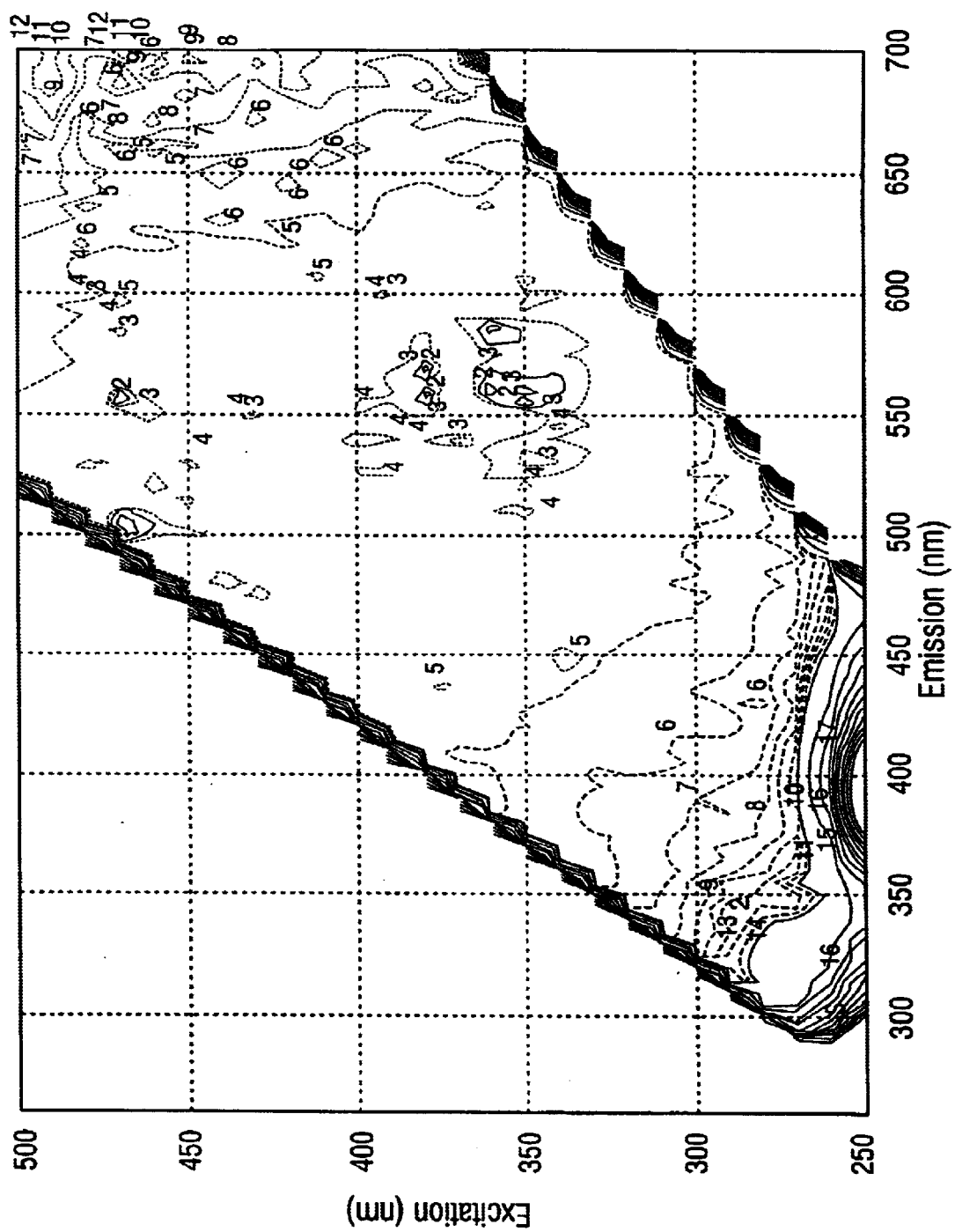

In addition, the transmission and fluorescence of FEP tubing (the presently preferred material for use as the housing for the probes of the present invention) was measured and the results are presented in FIGS. 16 and 17. As can be seen with reference to FIGS. 16 and 17, the fluorescence of the FEP tubing is low. However the autofluorescence of the FEP tubing is about ¹/₁₀ of the tissue fluorescence at 337 nm excitation. There is a main emission peak at 400 nm with 320 nm excitation. It was determined that this contribution could be accommodated during a probe calibration procedure, discussed in more detail below.

Clinical Procedure

In a clinical application, the present invention has as its purpose the characterization of epithelial viscus tissue, such as, for example, tissue of the endocervical canal. In general, when applied to the characterization of endocervical tissue, the present invention has as its purposes to: a) identify lesions extending from the ectocervix into the endocervical canal; b) detect the position of the transformation zone if present inside the endocervical canal; and c) identify squamous lesions with columnar involvement inside the endocervical canal. In general, these purposes are accomplished by measuring fluorescence spectra at spatially resolved locations inside the endocervical canal over a substantially cylindrical area of the interior surface of the tissue of the canal, and using mathematical models to characterize that tissue as a function of the measured spectra.

Before beginning a clinical procedure, the measuring apparatus should be calibrated. To calibrate the present invention (as shown, for example in FIGS. 1 and 2), the background signals are obtained without any excitation which reflects the dark current of the device. This background is stored and is automatically subtracted from any fluorescence measurement. Next, the autofluorescence of the probe is determined, for example, by placing the probe in a brown bottle containing sterile H2O and measuring fluorescence spectra with the excitation light on. This signal is not subtracted from the tissue fluorescence, however it may be subtracted if desired. In order to confirm calibration, a standard rhodamine solution (OD 0.446725, (=550 nm, 1 cm pathlength) may be measured. Based on previous clinical work, Rhodamine has been shown to have approximately twice the intensity of squamous cervical tissue fluorescence.

During spectral measurement of tissue, if improvement in the signal to noise ratio is desired, the spectra may be accumulated 100 and 200 times, respectively at 380 and 460 nm At 337 nm 50 accumulations have proven sufficient. However, other methods to improve the signal to noise ratio may also be used. For all three wavelengths a different background subtraction file may be used with the corresponding accumulations.

During a clinical procedure, it is desired to obtain fluorescence spectra at 3 excitation wavelengths along the substantially cylindrical surface of the entire endocervical canal with a spatial resolution of approximately 1.5 mm. This may be accomplished by use of either of the apparatus of FIG. 1 or 2, using any of the optical probes of FIGS. 4–12. During a procedure, the outer housing of the probe is placed and advanced to the internal os of the endocervical canal. Fluorescence measurement are then started. In the case of the single pixel probe (FIGS. 4 and 5), the single measuring pixel is advance both axially and angularly within the housing in order to image a sufficient number of pixels over the substantially cylindrical tissue surface. When using the ring probe (FIGS. 6–11), the measuring ring of pixels is advance axially in order to image a sufficient number of pixels over the substantially cylindrical tissue surface. Finally, when using the line probe (FIG. 12), the measuring line of pixels is incremented angularly in order to image a sufficient number of pixels over the substantially cylindrical tissue surface For example, when using the line probe, four individual measurement may be taken, one each at 12, 3, 6, and 9 o'clock (i.e., every 90°). This procedure takes approximately 3 minutes to complete.

Either before or during a procedure, saline solution may be flushed over the tissue in order possibly to improve measurement accuracy by removing mucus or blood or loose tissue form the measurement site.

In general, if the margin of the first specimen at the endocervical side is free of dysplasia or cancer and the second specimen shows no changes it may be assumed that the canal is in a normal condition. If this margin is involved with changes it may be assumed that the first 5 mm of the canal are in an abnormal state. If the margin of the endocervical specimen contains no changes it may be assumed that the margins extend no deeper than 2 cm. If this specimen shows abnormal cells it may be assumed that the measurements in the canal were abnormal even after 5 nm. If the second specimen is marked as metaplasia it may be assumed that the transformation zone is inside the endocervical canal. If the first specimen shows metaplasia the transformation zone is located around the os or on the ectocervix.

Figure 18:
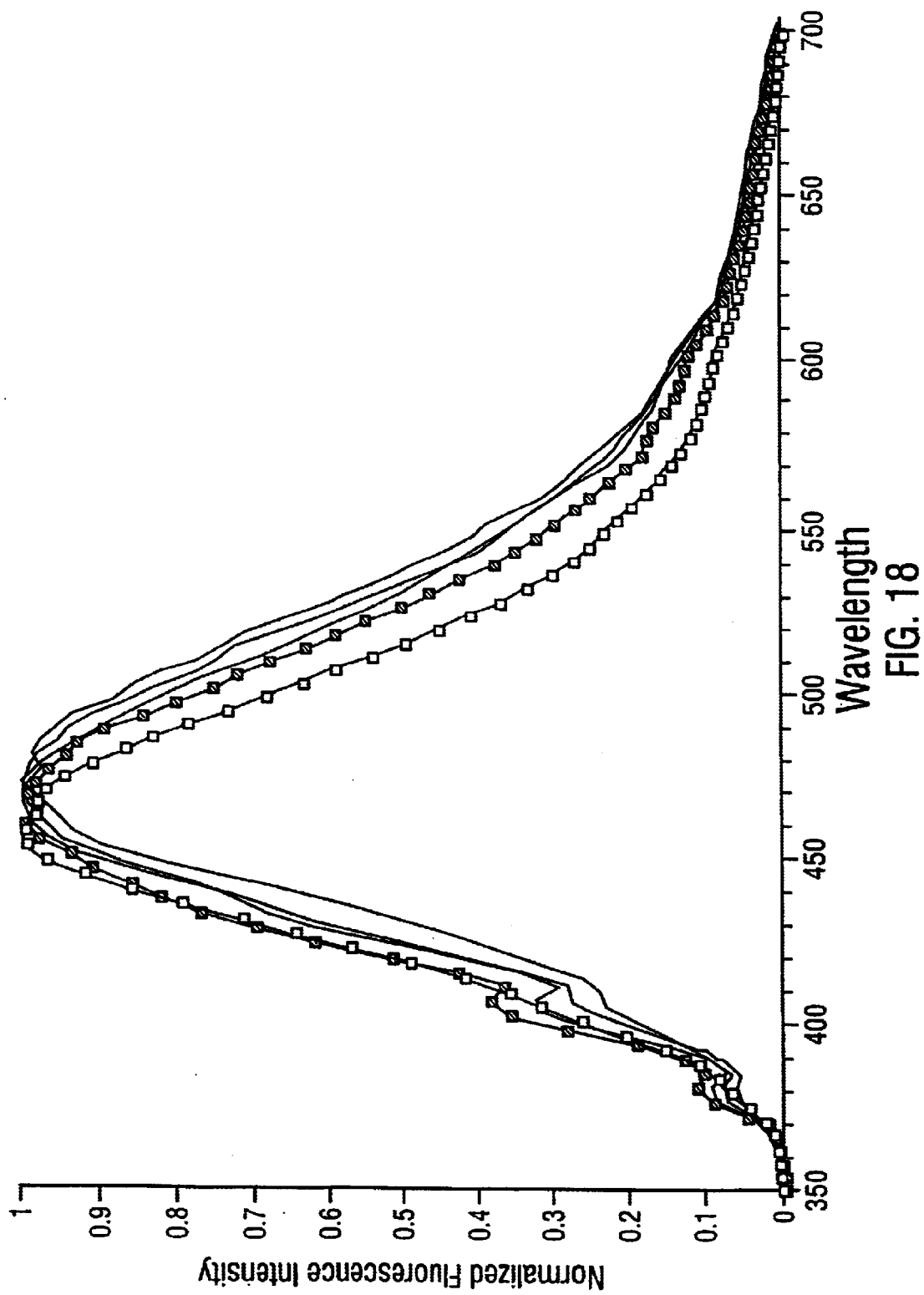
FIGS. 18, 19 and 20 are exmplary fluoresence spectra obtained from endocervical canal tissue.
Figure 19:
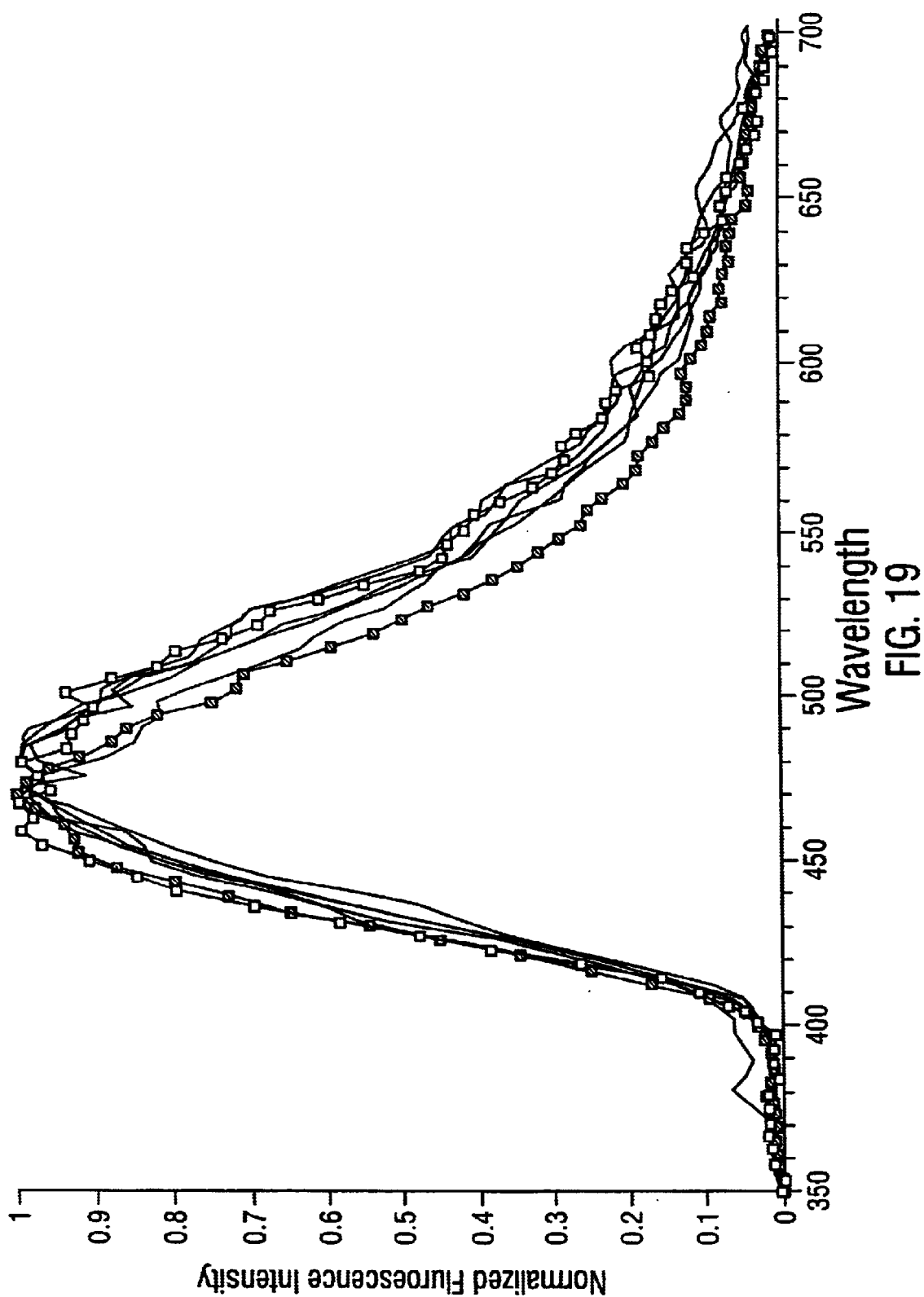
Figure 20:
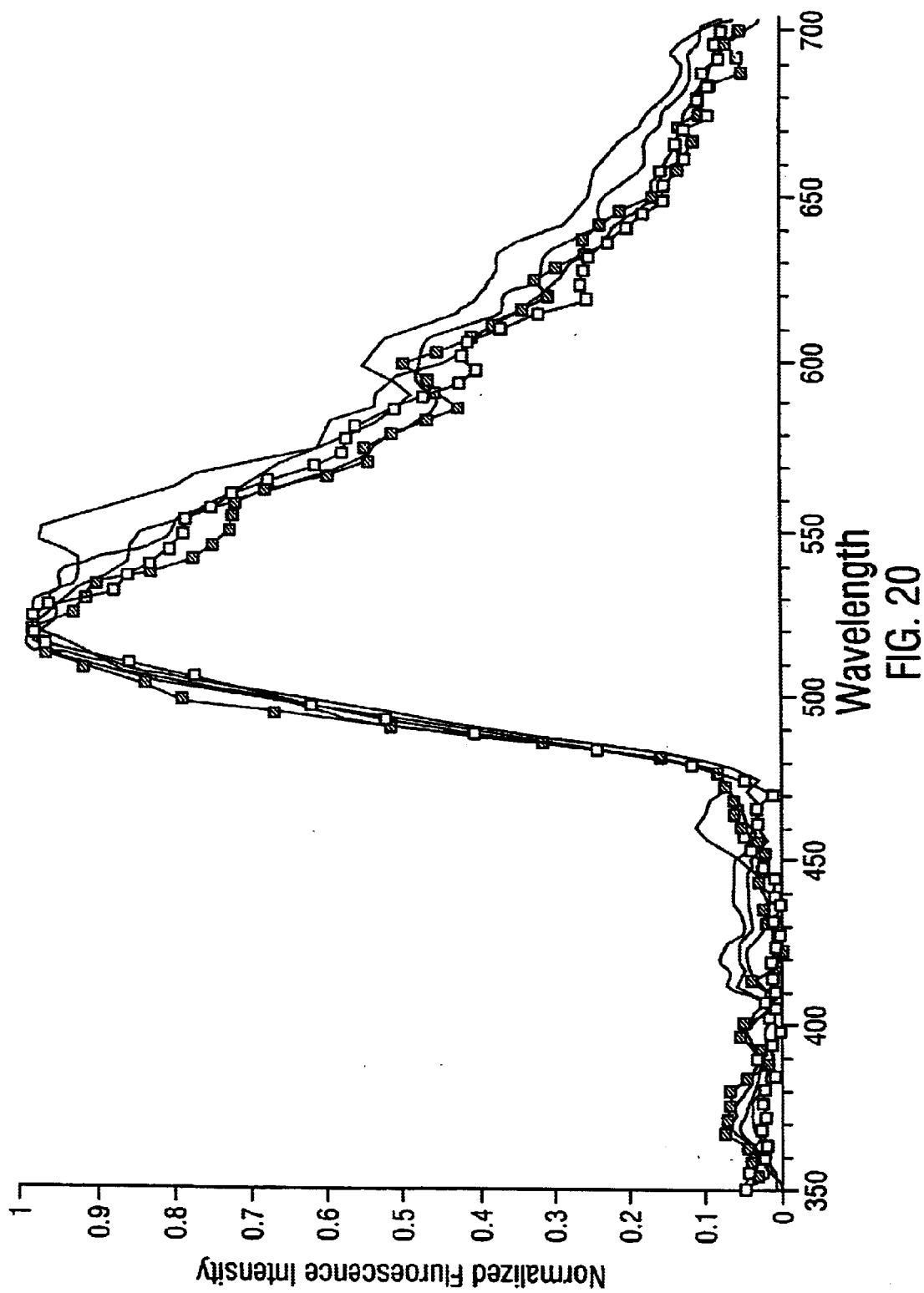

FIGS. 18, 19 and 20 present groups of normalized fluorescence intensity spectra obtained in vivo from endocervical canals of several different patients using the method and apparatus of the present invention In particular, FIG. 18 is a group of normalized fluorescence intensity spectra obtained with 337 nm excitation, FIG. 19 is a group of fluorescence intensity spectra obtained using 380 nm excitation, and FIG. 20 is a group of normalized fluorescence intensity spectra obtained using 460 nm excitation.

Based upon the foregoing disclosure, these and other features and advantages of the present invention will become apparent to those of ordinary skill in this art and it will be appreciated that additions, deletions and changes nay be made to the disclosed embodiments without departing from the scope of the invention.

The following references, to the extent that they provide exemplary experimental details or other information supplementary to that set forth herein, are incorporated by reference:

1. Wright T C, Kurman R J, and Ferenczy A in *Pathology of the Female Genital Tract* (eds. A. Blaustein), 156–177, Springer-Verlag, New York (1994).
2. Barron B A, Richart R M, "Statistical model of the natural history of cervical carcinoma: II. Estimates of the transition time from dysplasia to carcinoma in situ," JNCI 45: 1025–1030 (1970).
3. Burke L, Antonioli D A and Ducatman B S., *Colposcopy, Text and Atlas,* Appleton and Large, Norwalk Conn. (1991).
4. Mitchell M F, "Diagnosis and Treatment of Preinvasive Disease of the Female Lower Genital Tract" The Cancer Bulletin. 42: 71–76 (1990).
5. Reid R, Stanhope C R, Herschman B R, Crum C P, Agronow S J, "Genital warts and Cervical cancer," Am J Obstet Gynecol, IV: 815–823 (1984).
6. Reid R, Scalzi P, "Genital Warts and Cervical Cancer," Am J Obstet Gynecol, 153(6): 611–618 (1985).
7. Barrasso R, Coupez F, Ionesco M, DeBrux J, "Human Papilloma Viruses and Cervical Intraepithelial Neoplasia:

The Role of Colposcopy," Gynecologic Oncology, 27: 197–207 (1987).
8. Alfano R R, Pradhan A and Tang C G, "Optical spectroscopic diagnosis of cancer in normal and breast tissues," J Optic Soc Am B, 6: 1015–1023 (1989).
9. Andersson E S, Johansson J, Svanberg K and Svanberg S, "Fluorescence imaging and point measurements of tissue: applications to the demarcation of malignant tumors and atherosclerotic lesions from normal tissue," Photochem Photobiol, 53: 807–14 (1991).
10. Richards-Kortum R R, Rava R P, Petras R E, Fitzmaurice M, Sivak M V and Feld M S, "Spectroscopic diagnosis of colonic dysplasia," Photochem Photobiol, 53: 777–786 (1991).
11. Rava R P, Richards-Kortum R R, Fitzmaurice M, Cothren R M, Petras R E, Sivak M and Feld M S, "Early detection of dysplasia in colon and urinary bladder tissue using laser-induced fluorescence", Optical methods for tumor treatment and early diagnosis: mechanisms and technique, SPIE 1426: 68–78 (1991).
12. Wong P T T, Wong R K, Caputo T A, Godwin T A and Rigas B, "Infrared spectroscopy of human cervical cells: Evidence of extensive structural changes during carcinogenesis," Proc Natl Acad Sci USA, 88: 10988–10992 (1991).
13. Alfano R R, Lui C H, Sha W L, Zhu H R, Akins D L, Cleary J, Prudente R and Cellmer E, "Human breast tissues studied by IR fourier transform Raman spectroscopy," Lasers in Life Sc, 4: 23–28 (1991).
14. Baraga J J, Feld M S and Rava R P, "Rapid near-infrared Raman spectroscopy of human tissue with a spectrograph and CCD detector." Appl. Spectr, 46: 187–190 (1992).
15. Schomacker K T, Frisoli J K, Compton C C, Flotte T J, Richter J M, Nishioka N S and Deutsch T F, "Ultraviolet laser-induced fluorescence of colonic tissue: Basic biology and diagnostic potential," Lasers in Surg Med, 12: 63–78 (1992).
16. Mahadevan A, Mitchell M F, Thomsen S, Silva E and Richards-Kortum R R, "A study of the fluorescence properties of normal and neoplastic human cervical tissue," Lasers Surg Med 13:647–655, (1993).
17. Ramanujam N, Mitchell M F, Mahadevan A, Thomsen S, Malpica A, Wright T C, Atkinson, N and Richards-Kortum; In Vivo Diagnosis of Cervical Intraepithelial Neoplasia Using 337 Excitation, PNAS 91:10193, 1994.
18. Ramanujam N, Mitchell M F, Mahadevan A, Thomsen S, Richards-Kortum R R, "Spectroscopic Diagnosis of Cervical Intraepithelial Neoplasia (CIN) in vivo Using Laser Induced Fluorescence Spectra at Multiple Excitation Wavelengths," Lasers Surg Med, (in press) (1996).
19. Brookner C K, Agrawal A, Trujillo E V, Mitchell M F and Richards-Kortum R R, "Relative Risk of UV-Fluorescence Spectroscopy and Endoscopy are comparable," 24th. Annual Meeting of the American Society for Photobiology, Photochem Photobiol Supp. (in press) (1996).

What is claimed is:

1. A ring probe for applying a plurality of electromagnetic radiation wavelengths to an interior surface of endocervical canal tissue under test and for gathering fluorescence emitted from the tissue under test, the probe comprising:
   a plurality of optical fibers coaxially arranged in a ring shape;
   a reflector in operative relationship with the plurality of optical fibers, said reflector adapted to direct light from the probe in a substantially elliptical pattern; and
   a flushing channel extending through said probe, said channel adapted to flush the tissue under test.

2. The probe of claim 1, further comprising a first tubing surrounding said plurality of optical fibers, said first tubing being substantially transparent to visible and ultraviolet light.

3. The probe of claim 2, further comprising a second tubing surrounding said first tubing.

4. The probe of claim 1, wherein the reflector comprises a metal plug comprising a polished reflecting surface.

5. The probe of claim 1, wherein the reflector comprises a sapphire tip.

6. The probe of claim 1, wherein the reflector comprises cleaved and polished optical fibers.

* * * * *